(12) United States Patent
Moles et al.

(10) Patent No.: US 7,328,619 B2
(45) Date of Patent: Feb. 12, 2008

(54) PHASED ARRAY ULTRASONIC NDT SYSTEM FOR FASTENER INSPECTIONS

(75) Inventors: Michael Moles, Toronto (CA); Olivier Dupuis, St-Augustin-de-Desmaures (CA); Fabrice Cancre, Lexington, MA (US); Pamela Herzog, Jones, OK (US); James Ted Miller, Marrietta, GA (US); Jamie Hatmaker, Cedartown, GA (US)

(73) Assignee: R/D Tech Inc., Quebec (CA)

( * ) Notice: Subject to any disclaimer, the term of this patent is extended or adjusted under 35 U.S.C. 154(b) by 0 days.

(21) Appl. No.: 10/209,298

(22) Filed: Jul. 30, 2002

(65) Prior Publication Data

US 2004/0020296 A1    Feb. 5, 2004

(51) Int. Cl.
*G01N 29/07*    (2006.01)

(52) U.S. Cl. .............................. 73/598; 73/619; 73/620; 73/622

(58) Field of Classification Search .................. 73/598, 73/600, 1.29, 622, 628, 629, 638, 637, 761, 73/618, 619, 620
See application file for complete search history.

(56) References Cited

U.S. PATENT DOCUMENTS

| | | | | |
|---|---|---|---|---|
| 3,977,236 A | * | 8/1976 | Raatz et al. | 73/614 |
| 4,052,889 A | * | 10/1977 | Mucciardi et al. | 73/602 |
| 4,095,181 A | * | 6/1978 | Harris et al. | 324/238 |
| 4,322,975 A | * | 4/1982 | Schmidt et al. | 73/633 |
| 5,095,753 A | * | 3/1992 | Russ et al. | 73/598 |
| 5,156,050 A | * | 10/1992 | Schmid et al. | 73/628 |
| 5,708,208 A | * | 1/1998 | Bonitz | 73/644 |
| 6,186,010 B1 | * | 2/2001 | Eguchi et al. | 73/761 |
| 6,796,182 B2 | * | 9/2004 | Wagner et al. | 73/588 |

FOREIGN PATENT DOCUMENTS

GB        2292610 A    *  2/1996

OTHER PUBLICATIONS

Selman et al., "A Novel Fastener Hole Inspection Method Using an Ultrasonic Phased Array Probe", Sep. 2001, pp. 1-13.*
Moles et al., "Inspection of Fastener Holes Using Ultrasonic Phased Arrays," *2000 USAF Aircraft Structural Integrity Program Conference*, Dec. 2000, San Antonio, Texas, 32 sheets.
Lupien et al., "Three-Dimensional Imaging of Fastener Holes Using Ultrasonic Phased Arrays," *Poster Session for Review of Progress in Quantitative NDE*, Jul. 2000, Ames, Iowa, 2 sheets.

(Continued)

*Primary Examiner*—Hezron Williams
*Assistant Examiner*—Nashmiya Fayyaz
(74) *Attorney, Agent, or Firm*—Ostrolenk, Faber, Gerb & Soffen, LLP

(57) ABSTRACT

An ultrasonic probe suited for testing the integrity of sheet metal surfaces around fastener openings is provided with means to center the probe over such openings. Both a mechanical centering rod and an electronic display assist the user in centering such probe. Once positioned within tolerance limits, phased array ultrasonic beams search for defects within the metal surfaces, allowing for residual offsets in the centering of the probe. Also described are test fixtures for calibrating the probe.

27 Claims, 24 Drawing Sheets

OTHER PUBLICATIONS

Lupien et al., "Three-Dimensional Ultrasonic Phased Array Imaging for Fastener Inspections," *The Fourth Joint DoD/FAA/NASA Conference on Aging Aircraft*, May 2000, St. Louis, Missouri, 13 sheets.

Selman et al., "Inspection of Aircraft Fastener Holes Using a Conically Shaped Multi-Element Phased Array Probe," *28th Annual Review of Progress in Quantitative Nondestructive Evaluation Conference*, Jul.-Aug. 2001, Maine, 36 sheets.

Selman et al., "Review of Progress in Quantitative Nondestructive Evaluation," *Center for NDE and Department of Aerospace Engineering and Engineering Mechanics, Iowa State University, AIP Conference*, vol. 21A, Jul.-Aug. 2001, Maine, pp. 886-893.

www.ob-ultrasound.net.linearrays.htm "Linear Array Transducer," 3 sheets.

* cited by examiner

PHASED ARRAY ULTRASONIC NDT SYSTEM FOR FASTENER INSPECTIONS

FIELD OF THE INVENTION

This invention relates to the non-destructive testing of materials surrounding fastener holes using ultrasonic phased arrays. More particularly it relates to a device for positioning a testing assembly over fastener holes and the detection of corrosion and material defects in the materials surrounding such fastener holes. The invention is particularly useful for testing material surrounding fastener openings present in the skin of aircraft.

BACKGROUND TO THE INVENTION

There has long been a requirement to detect small cracks and defects present on the faying surfaces of aircraft wing skin material present around fastener holes formed therein. This procedure is carried out with the fastener installed in the fastener opening. Aircraft fastener holes are prone to developing cracks that can propagate and result in serious structural failure.

The current system has been in service for many years, but is now obsolescent and no longer maintainable. Its drawbacks include a mechanically-complex scanner that requires the physical rotation of two conventional single-element ultrasonic probes (sequentially—one in each direction around the entire circumference of the hole) that requires a long inspection time of up to several minutes per fastener hole. Further, it is necessary to center the scanner very precisely over the hole, which contributes to the length of the inspection, particularly because the scanner is of such weight that it must be supported by a floor stand when conducting under-wing inspections.

One known way to improve upon this system is to utilize a matrix of ultrasonic elements arrange in a conical configuration encircling the fastener head. This arrangement permits deflection of the ultrasonic beams it forms in three dimensions, and adapts to different hole diameters and skin thicknesses. Initial approaches to this solution were described in the following three papers: (1) *Inspection of Fastener Holes Using Ultrasonic Phased Arrays* by Moles, Lamarre, Selman, Miller and Herzog presented at the 2000 USAF Aircraft Structural Integrity Program Conference, December 05-07 in San Antonio, Tex.; (2) *Three-Dimensional Imaging of Fastener Holes Using Ultrasonic Phased Arrays* by Lupien, Moles, Selman, Miller and Herzog at the poster session for Review of Progress in Quantitative NDE, Jul. 17-21, 2000 in Ames, Iowa; and (3) *Three-Dimensional Ultrasonic Phased Array Imaging for Fastener Inspections* by Lupien, Moles, Selman, Miller and DoD/FAA/NASA Conference on Aging Aircraft Conference, May 15-18, 2000 in St. Louis, Mo.

Two later and more detailed descriptions of the technology are contained in (1) *Inspection of Aircraft Fastener Holes Using a Conically Shaped Multi-Element Phased Array Probe* by Selman, Miller, Moles, Dupuis and Herzog presented at the 28th Annual Review of Progress in Quantitative Nondestructive Evaluation Conference held in Brunswick, Me. Jul. 29-Aug. 3, 2001 and subsequently published in Volume 21A of the proceedings of the conference; and (2) *A Novel Fastener Inspection Method Using an Ultrasonic Phase Array Probe* by Selman, Miller, Moles, Dupuis and Herzog at the Aging Aircraft 2001 Conference, Sep. 10-14, 2001.

Essentially, phased arrays ultrasonic systems generate focused beams by controlling the timing of the emission of sound waves generated from a plurality of separately spaced piezoelectric elements. Not only can focused beams of ultrasonic waves be formed, but such beams may be directed within a volumetric working space to probe for discontinuities in the media transmitting the sound waves. Defects beneath the surface of an aircraft wing surrounding a fastener are detectable on the basis of sonic echoes that are returned or deflected from such discontinuities. As phased array beams are generated electronically, electronic scanning permits very rapid inspections of structural components that have uniform geometries.

A need exists for a handheld, lightweight, portable crack detection system that can be rapidly positioned over fasteners, and then can rapidly detect faying surface cracks in the first layer around the base of a fastener hole with the fastener installed.

Objects of the invention are therefore to provide a means for positioning a phased array ultrasonic probe centrally over a cylindrical hole in a surface to be tested; and means to detect defects in the materials surrounding the hole efficiently and reliably using phased array ultrasonic technology.

The invention in its general form will first be described, and then its implementation in terms of specific embodiments will be detailed with reference to the drawings following hereafter. These embodiments are intended to demonstrate the principle of the invention, and the manner of its implementation. The invention in its broadest and more specific forms will then be further described, and defined, in each of the individual claims that conclude this Specification.

SUMMARY OF THE INVENTION

The invention builds upon the concept of a matrix of ultrasonic elements arranged in a conical configuration encircling the fastener head as described in the prior art (see reference in Background to the Invention above). As already stated, this arrangement permits deflection of the ultrasonic beams it forms in three dimensions, and adapts to different hole diameters and skin thicknesses. A full circumferential scan of the faying surface of a fastener hole is performed without removal of the fastener using a preprogrammed sequence of phased array focal laws. The preferred inspection method uses pulse-echo at a variety of angles incident on a suspected crack to thoroughly cover the fastener hole and surrounding area, and it is designed to detect cracks as small as 0.030 of an inch in length. The invention can also be operated using a pitch-catch mode of inspection.

According to one aspect of the invention, to assist in the initial manual alignment of the ultrasonic probe of the invention, the probe assembly may be provided with a central, spring-loaded alignment rod that may be placed on a fastener. Depression of this rod into the probe assembly casing will cause the probe assembly to descend upon the fastener, landing with the assembly approximately positioned centrally over the fastener.

This centering rod is positioned centrally with respect to the conic array of elements, located inside a sleeve formed in a variant on the standard "boot" used in ultrasonic devices. This boot is fitted to the forward end of the conic probe with its flanges firmly anchored to the probe housing. As the boot is donut-like in shape, it is able to contain water to provide an acoustic transmission column for the ultrasonic beams, while permitting the centering rod freedom to move within the central sleeve.

According to a further feature of the invention, an operator-assisting positioning system is preferably provided in the form of four illuminated sources (e.g., light emitting diodes) arranged in the pattern of a cross. When all four sources are lit, the operator is informed that centering within a preset tolerance limit has been achieved. Otherwise, the illumination of a single source provides a signal that the probe assembly should be displaced in the direction of the illumination. When two contiguous sources are illuminated, a signal is provided that the probe assembly should be displaced in an oblique direction, passing between the two illuminated sources. In this manner, an operator is given a ready indication as to positioning the probe assembly substantially centrally over the fastener opening to be tested. Once the probe is within 0.030 of an inch of being centered, no further centering is needed. Using phased array ultrasonic examination, the exact position of the probe with respect to the fastener can be determined and, using its steering ability, the system can compensate for the residual positioning error while performing the scan.

Data for the operation of the operator-assisting positioning system is obtained through the use of at least three phased array ultrasonic beams that locate points on the cylindrical surface of the fastener opening at a common depth below the surface of the skin within which such opening is formed. Initially, such beams sweep through the volume of the skin to locate the cylindrical surface. Once a scan detects the boundary of the hole by the reflection of ultrasonic beams from the sides of the hole, the position of the source of this reflection is recorded as a point on the side of the cylindrical surface of the hole. Once three such points have been located, the location of the true center of the hole is determined by applying standard geometric procedures within a computer-based system controller. Positioning signals for the operator-assisting positioning system are then provided to guide the probe assembly into near-alignment with the center of the fastener opening.

According to a further feature of the invention, the probe assembly operates on the basis of a scan pattern wherein the focal points of more than one, preferably three, probing beams are directed to consecutive locations encircling the fastener opening, whereby each scanned location is sampled by more than one, preferably three, beams arriving at the sampled location along more than one, preferably three, distinct paths. To maximize the detection of cracks formed around the fastener opening, such beams are preferentially selected to arrive at the scanned location along paths that are generally tangentially oriented with respect to the side of the fastener opening.

As a preferred procedure, two sets of more than one probing beams are directed to a scanned location from opposite sides of the fastener opening, arriving along generally nearly tangential paths. More preferably, three beams are directed to the scanned location, arriving from opposite sides, so that a total of six beams are used to sampled each scanned location. Generally, and preferably, the sampled locations are equally spaced around the cylindrical opening.

This preferred scan pattern may commence initially with a path that follows the circumferential boundary of the cylindrical surface of the hole at the level of the faying surface. Second and, optionally, third scanning patterns are then preferably effected along encircling paths located at a progressively greater radius from the center of the fastener opening. Optionally, and preferably, these scanning locations may be located radially outwardly from the initial inspected points positioned around the side surface of the hole.

As a further feature of the invention a special test fixture is provided wherein a conically shaped target surface is provided having the same conic angle as that of the conic array. The individual element elements in the conic array are then actuated sequentially. The timing of the returning echoes arising from reflection of individual sonic emissions from the conical target surface is recorded as calibration data. This calibration data is then used to electronically correct for slight misalignments or miss-positioning of the individual elements in the conic array and to verify that the individual elements are functioning properly.

By a further feature of the invention, the solid conical target surface is substituted by a test block having a hole with an intentionally formed notch present in its side surface, which notch represents a fatigue crack. The block with the notch is mounted for 360-degree rotation. Rotation is then carried out in order to effect testing of the conic array for uniformity of response. To the extent that the array, and sets of elements therein, do not display a uniform response to such rotational positioning of the test notch, electronic corrections are subsequently provided by the phased array controller in the processing of array data in field testing to correct for the non uniformity in the response of the array and sets of elements.

The foregoing summarizes the principal features of the invention and some of its optional aspects. The invention may be further understood by the description of the preferred embodiments, in conjunction with the drawings, which now follow.

DESCRIPTION OF THE PREFERRED EMBODIMENT

Detection Requirement

Figures 1A, 1B:
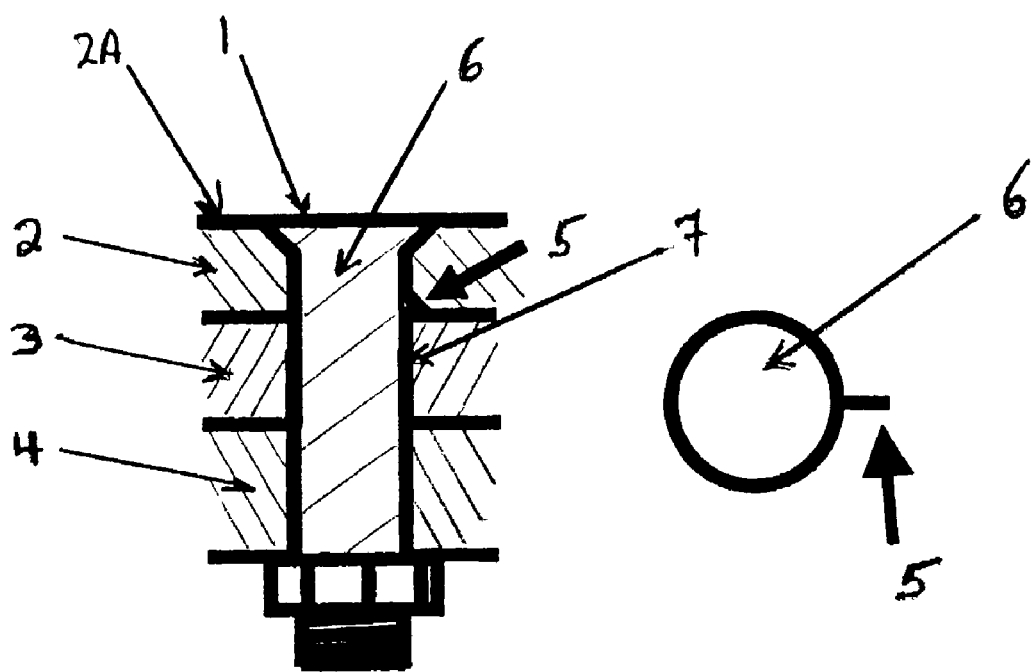
FIG. 1A is a side view cross-section illustration of the inspection requirement showing a typical faying surface crack.
FIG. 1B is a top view of the crack illustrated in FIG. 1A.

In the preferred embodiment of the invention, the object is to detect defects anywhere around the fastener hole wherein the defects are at least 0.030 of an inch in length. Typical fastener diameters range from 3/16 to 5/16 of an inch and skin thicknesses from 0.117 to 0.310 of an inch. FIG. 1A illustrates fastener 1 holding together layers 2, 3 and 4 of, typically, aluminum with faying surface crack 5 in first skin layer 2. FIG. 1B further illustrates crack 5 in a top view.

Scanning Using Phased Array Beams from Conic Surface

Figure 2:
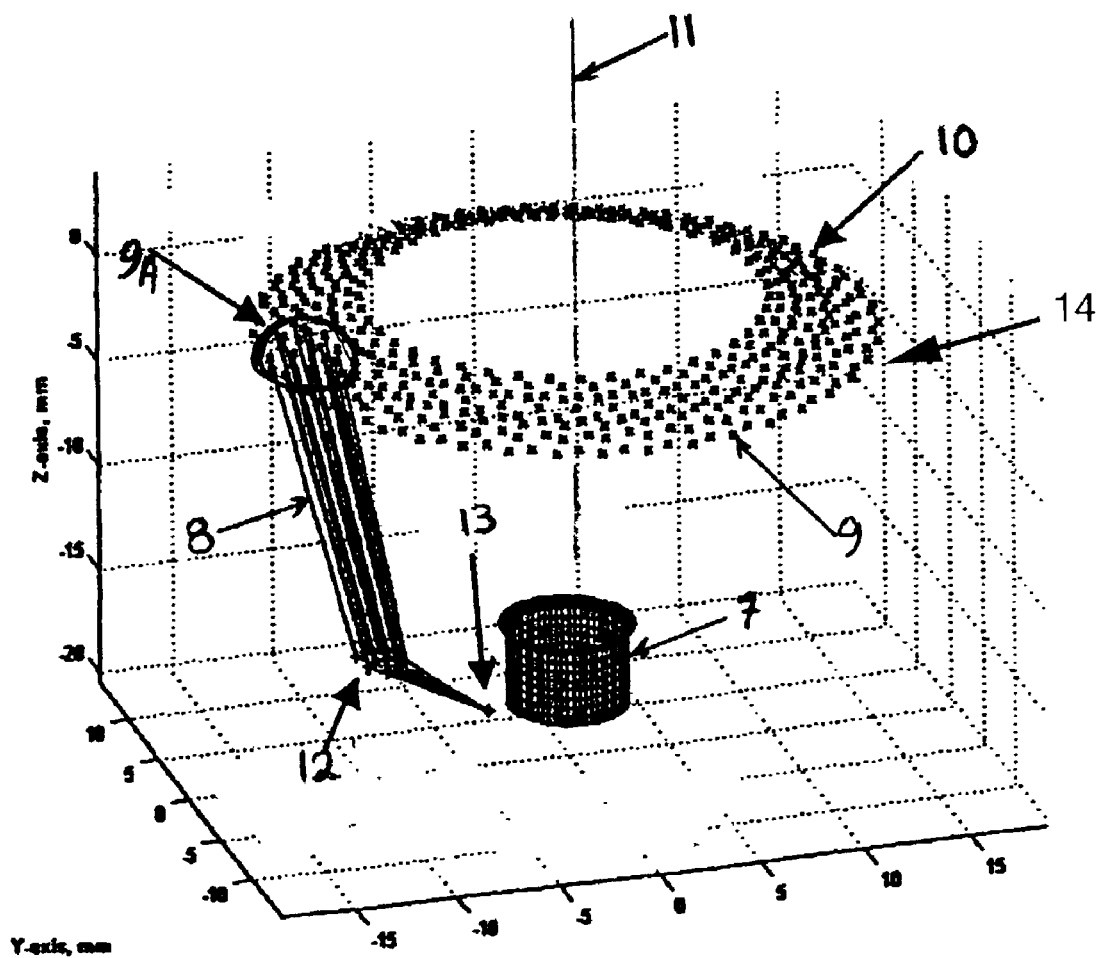
FIG. 2 is a schematic presentation of the probe element layout.

An angled beam is required in order to direct the ultrasonic beam under the fastener head 6 towards the fastener hole circumference 7 at the faying surface 2/3 interface. Phased array (PA) ultrasonic beams, as typified by beam 8, are preferably generated from a number of elements 9, typically piezoelectric crystals, distributed over a conic surface 10 that surrounds from above (i.e., looking down) a fastener opening placed beneath and substantially in alignment with the axis 11 of such conic surface 10. In the preferred embodiment, approximately 504 ultrasonic elements are distributed over this conic surface 10 to create conical probe 14, as illustrated in FIG. 2.

A water path (not shown in FIG. 2, but fully detailed below in FIG. 5) couples PA ultrasonic beam 8 with aluminum skin layer 1 at point 12, which is also the point of emergence of the beams at the water/aluminum skin interface on the top surface 2A of first skin layer 2 (see FIG. 1A). The focal point 13 of beam 8 is close to circumference 7, hence close to the anticipated location of cracks 1 (if any) at the faying surface 2/3 interface. Full circumferential scans are performed by programming groups 9A of elements 9 in sequence so that they fire successively around the conical probe 14, one such group 9A being illustrated in FIG. 2. In this way, they can scan around a fastener opening at the faying surface, using scan patterns that extend over a variety of angles and spatial volumes surrounding the perimeter of the hole.

Suppression of Grating Lobes

The suppression of grating lobes, which generate misleading false signals, was effected as initially described in the Aging Aircraft 2000 Conference referenced above in the Background to the Invention section. The design trade-off from an ultrasonic point of view was to select the largest number of elements possible while maintaining sufficient deflection power to generate the required beam angles for all the desired fastener diameters and skin thicknesses, using the smallest number of elements possible while still maintaining acceptably low grating lobes. Current state of the art in probe fabrication and cost/size restrictions on the PA electronics imposed a practical limitation of 512 elements 9 on conic surface 10 of conical probe 14.

Figure 3A:
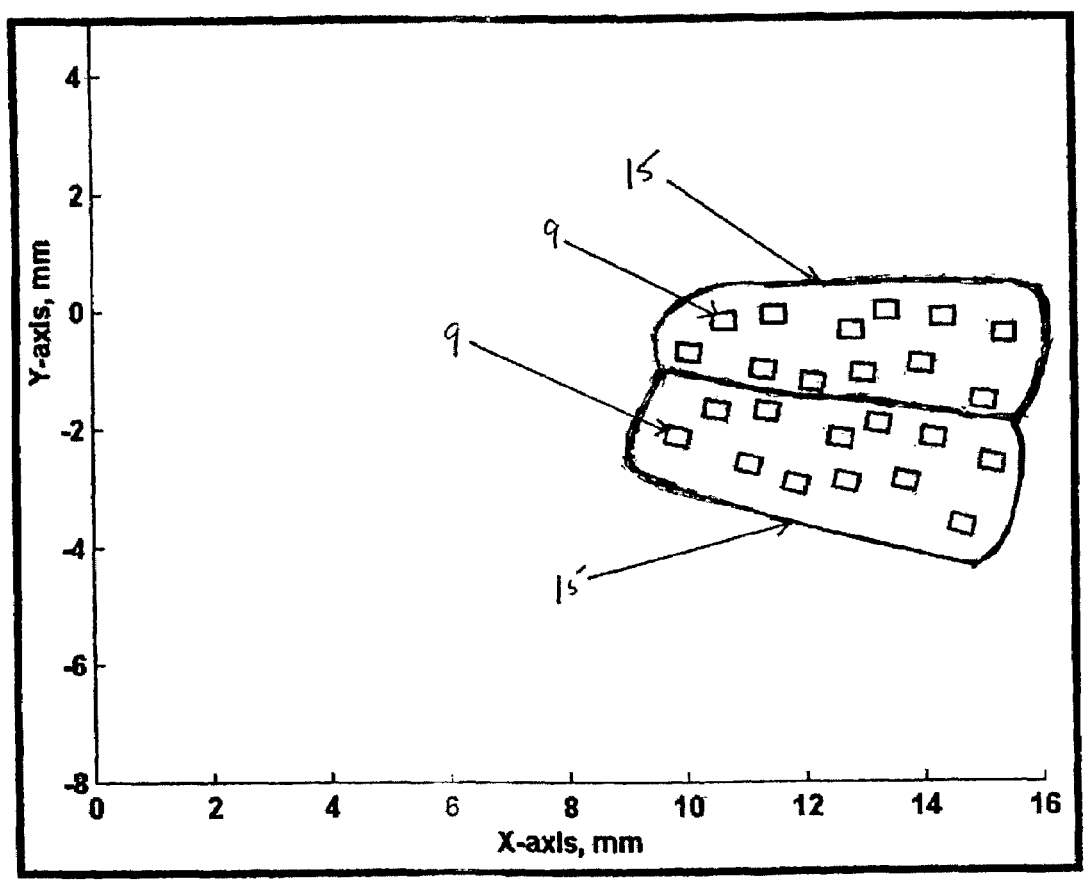
FIG. 3A depicts two of the 42 identical pseudo-random groups of 12-elements that make up the conic probe.
Figure 3B:
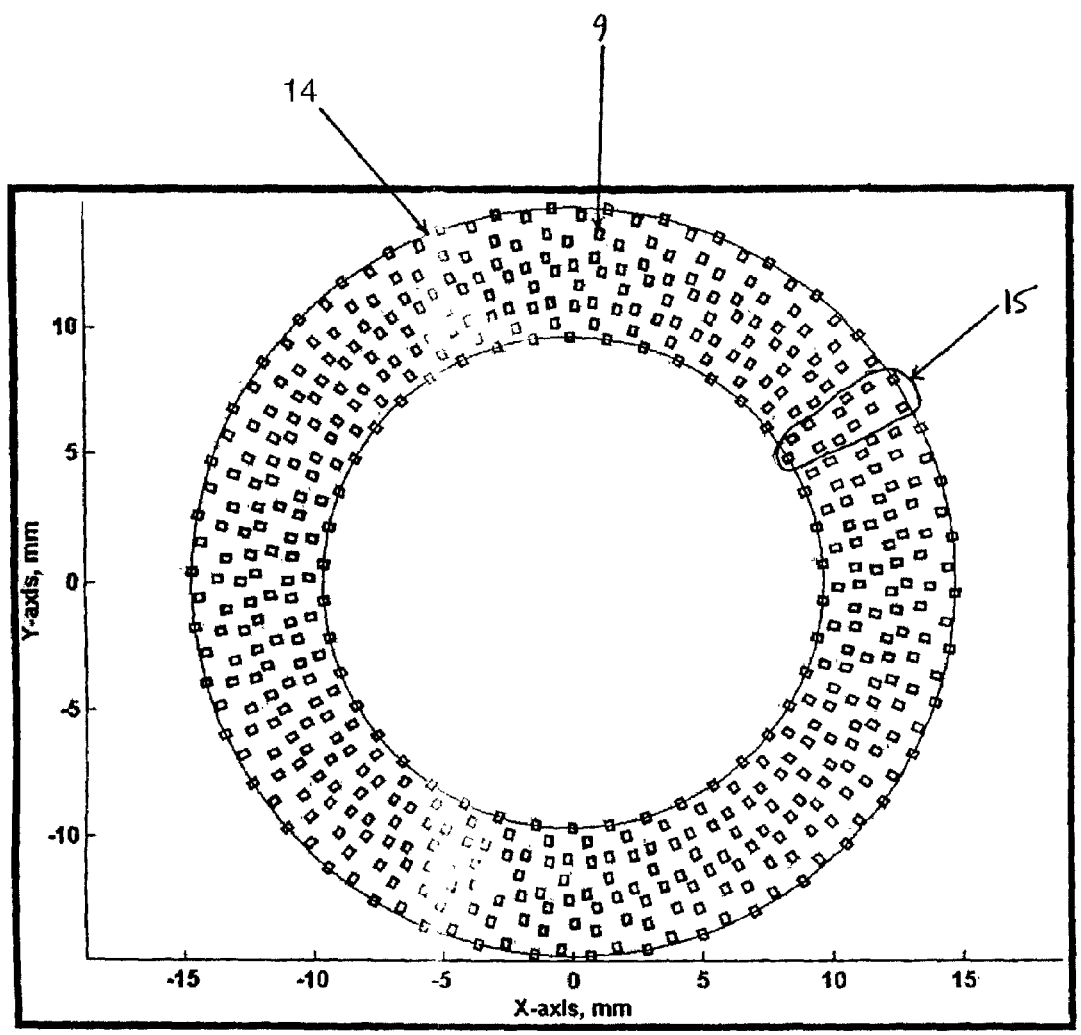
FIG. 3B shows the apparent randomness of the elements of the conic probe.

The classic strategy for reducing grating lobes to an acceptable level was adopted by randomizing the positions of the elements, thereby lowering their peak intensity. This was accomplished by forming pseudo-random groups 15 of 12 elements each, as shown in FIG. 3A, and then repeating such groups 15 a total of 42 times (i.e., 504 elements) around conical probe 14 to achieve the result illustrated in FIG. 3B. This randomness configuration of element spacing significantly reduced the peak grating lobe amplitudes by effectively spreading the grating lobe energy over a large spatial area, while maintaining practical manufacturability of the probe.

Formation of Phased Array Beams

Figure 4:
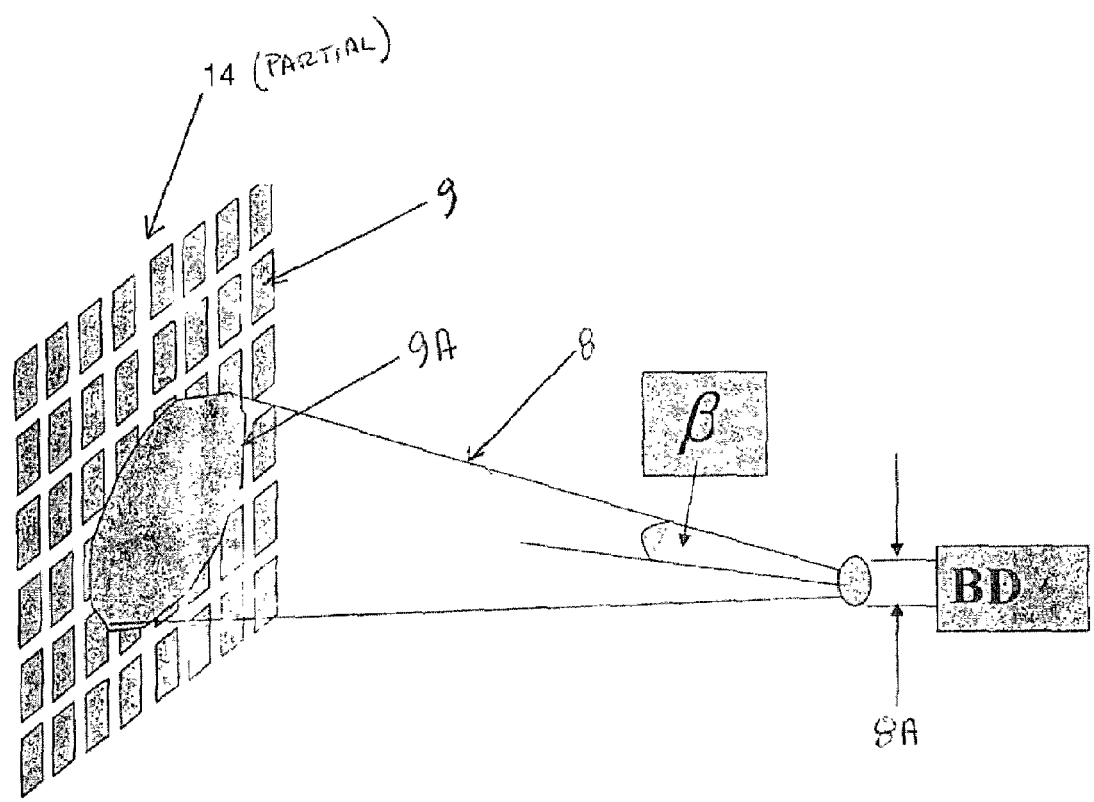
FIG. 4 is a sketch illustrating how element groupings for the formation of phased array beams are determined.

The number of elements that are active for each focal law (ultrasonic beam) is a function of the beam diameter at its focal point (BD) 8A, as shown in FIG. 4, which is 0.030 of an inch for the preferred inspection requirement. By working backwards using the angular cone of converging energy ($\beta$) and the wavelength $\lambda$, the intersection of the cone 8 with the conic surface 10 of conical probe 14 gives the approximate number of elements 9 required through the relation BD=$\lambda$/(2 tan $\beta$). These are the elements contained in group 9A in FIGS. 2 and 4. For the range of fastener hole sizes and skin thickness to be covered, the number of active elements 9 varies from 14 to 38.

Assembled Phased Array Probe Inspection System

Figure 5:
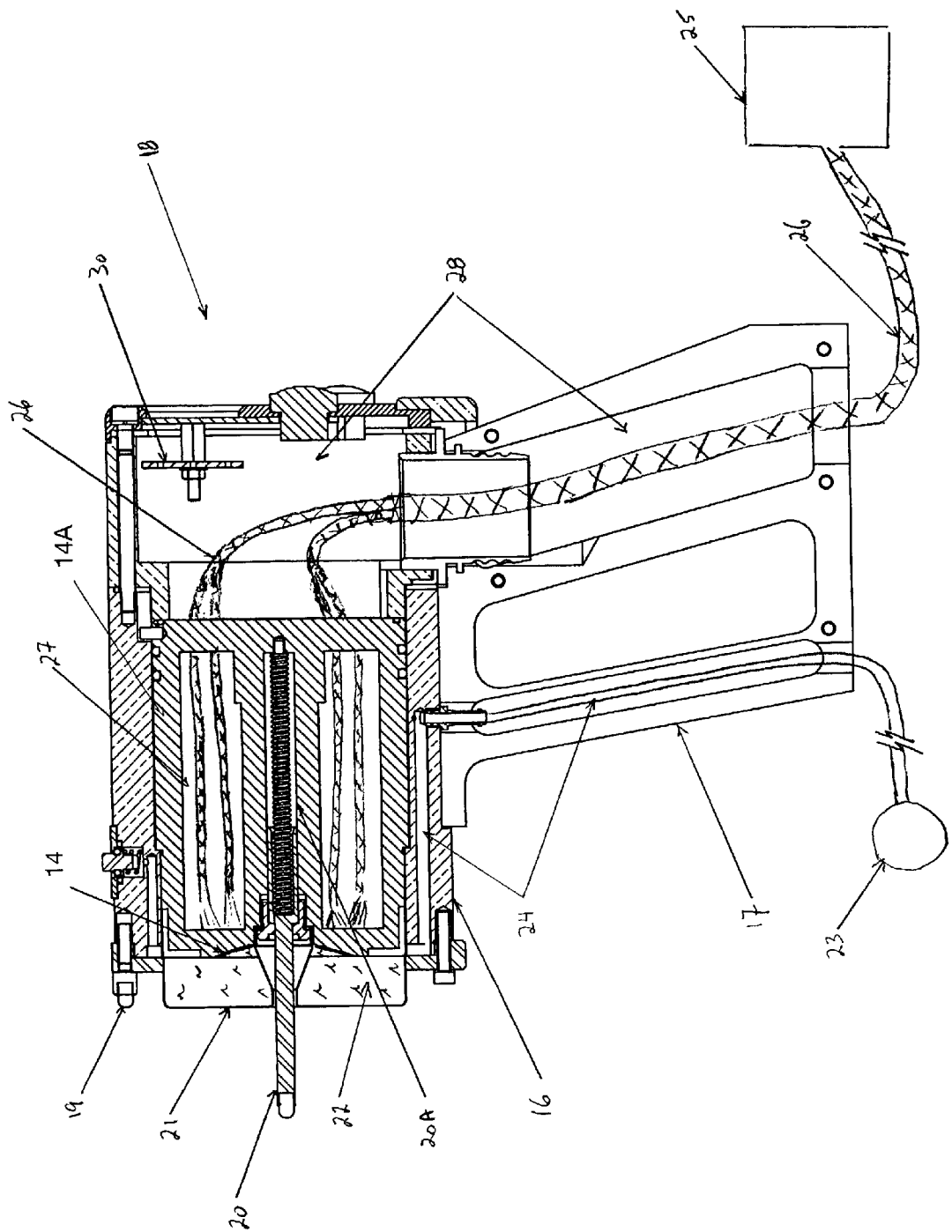
FIG. 5 is a cross section side view of the phased array probe system.

As detailed in FIG. 5, sub-assembly 14A containing conical probe 14 is first inserted into housing 16 and then hand grip 17 is added to form PA probe assembly 18. In the preferred embodiment, there are three feet 19, preferably of Teflon™, on the outer circumference of, and normal to, the forward face of PA probe 18 assembly (see also FIG. 7A). They are required to properly orient the conic surface 10 of conical probe 14 over fastener head 6. The length of PA probe assembly 18 is approximately 6.5 inches and the diameter of housing 16 is approximately 3.6 inches.

The centering rod 20 may be spring-loaded, and is used to assist in rough centering of the probe over the fastener head 6. The manner in which the PA probe assembly 18 is precisely centered prior to operation is described in full separately below.

Flexible boot 21, preferably made of latex, is filled with a coupling fluid 22, water in the preferred embodiment, which covers the entire conical surface 10 and the elements 9 located thereon during operation. Water 22 is provided to boot 21 by pump 23 through channel 24 in housing 16 and handgrip 17. Further details concerning boot 21 are also given separately below.

The 504 elements 9 on conical probe surface 10 of conical probe 14 are all individually connected to a remote system controller and data acquisition system 25 ("system controller" 25) via a single shielded cable 246. This is effected by first bundling the 504 wires into four groups of 126 wires in cabling assembly volumes 27 of sub-assembly 14A prior to being incorporated into a single cable 26 in volume 28s after passing through the rear of housing 16. Volumes 28 allow cable 26, which has now become somewhat unwieldy, to exit the PA probe assembly 18 through handgrip 17.

The preferred system controller 25 to drive the phased array probe and process the data is a FOCUS 32/256 unit, which is available commercially from R/D Tech Inc. of Quebec City, Canada. This off-the-shelf system controller is capable, in conjunction with a Windows NT operating system, of controlling and monitoring 256 element elements. Two such systems may be connected in a master-slave configuration to control up to 512 elements (504 are used in the preferred embodiment). In the configuration of the preferred embodiment, up to 64 element's may be activated by the FOCUS 32/256 unit at any one time to form an ultrasonic beam. More typically, as previously mentioned, 14 to 38 elements may be used to form a beam having a −6 dB focal spot width of approximately 0.030 of an inch.

Figure 6:
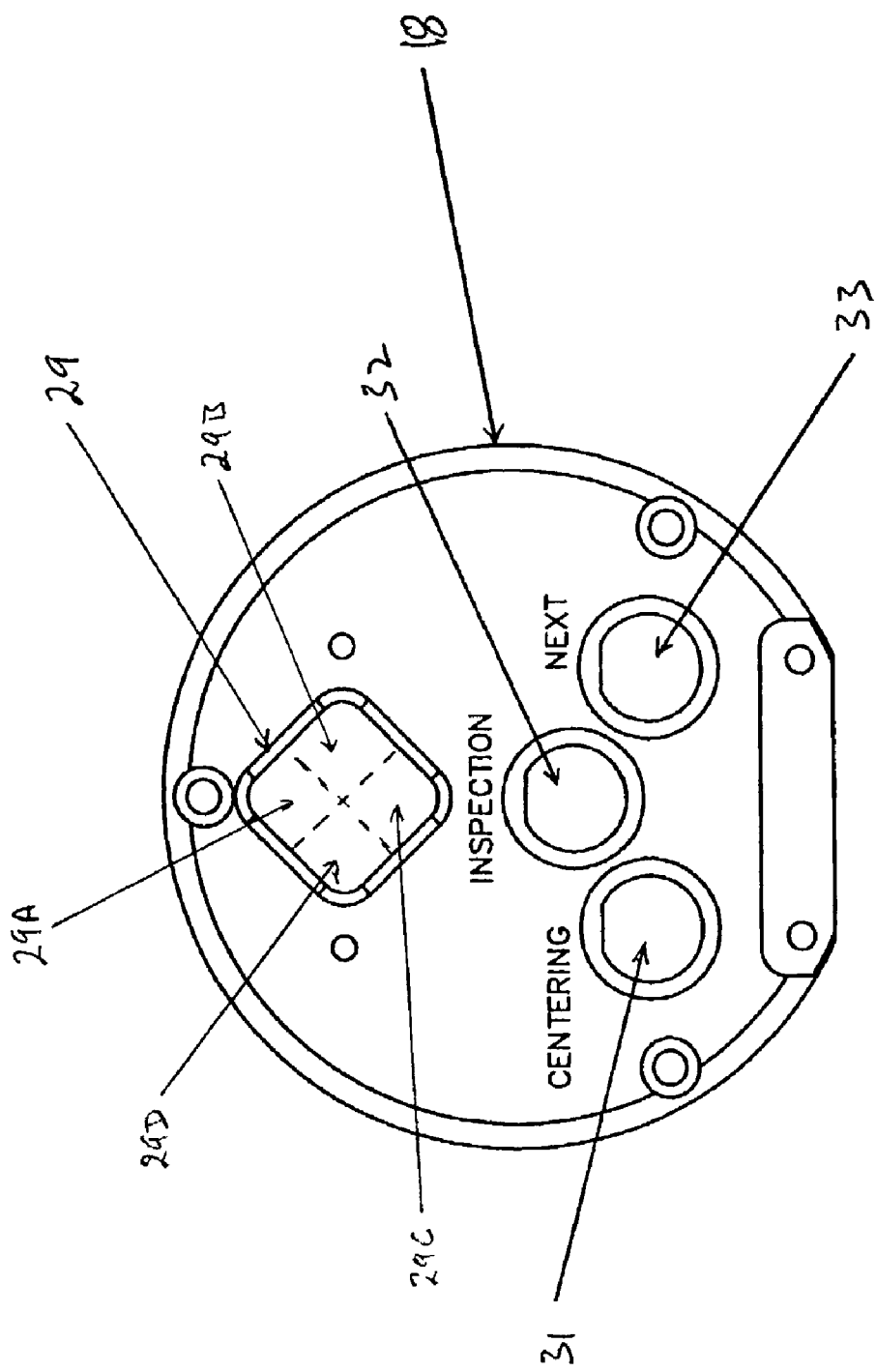
FIG. 6 is a rear view of the phased array probe system.

FIG. 6 is a rear view of PA probe assembly 18 showing a probe centering light emitting diode (LED) indicator screen 29 and three actuation buttons. Screen 29 has four sectors 29A, 29B, 29C and 29D, each of which can be independently illuminated. A portion of the electronics 30 for LED screen 29 are shown in FIG. 5, the remainder being located in system controller 25. Returning to FIG. 6, Centering button 31 is pushed to activate the probe-centering algorithm as explained below. Once centering is achieved (normally in fewer than 15 seconds), Inspection button 32 is activated and the inspection routine is completed in a further few seconds. The inspection technique and how it is effected is described separately in a third section below. Finally, the Next button 33 is pushed to indicate that inspection of the fastener hole is complete so that the location of the hole can be recorded by system controller 25 along with the inspection results before a new file is opened that will allow the same sequence to be repeated for the next fastener hole.

Figures 7A, 7B:
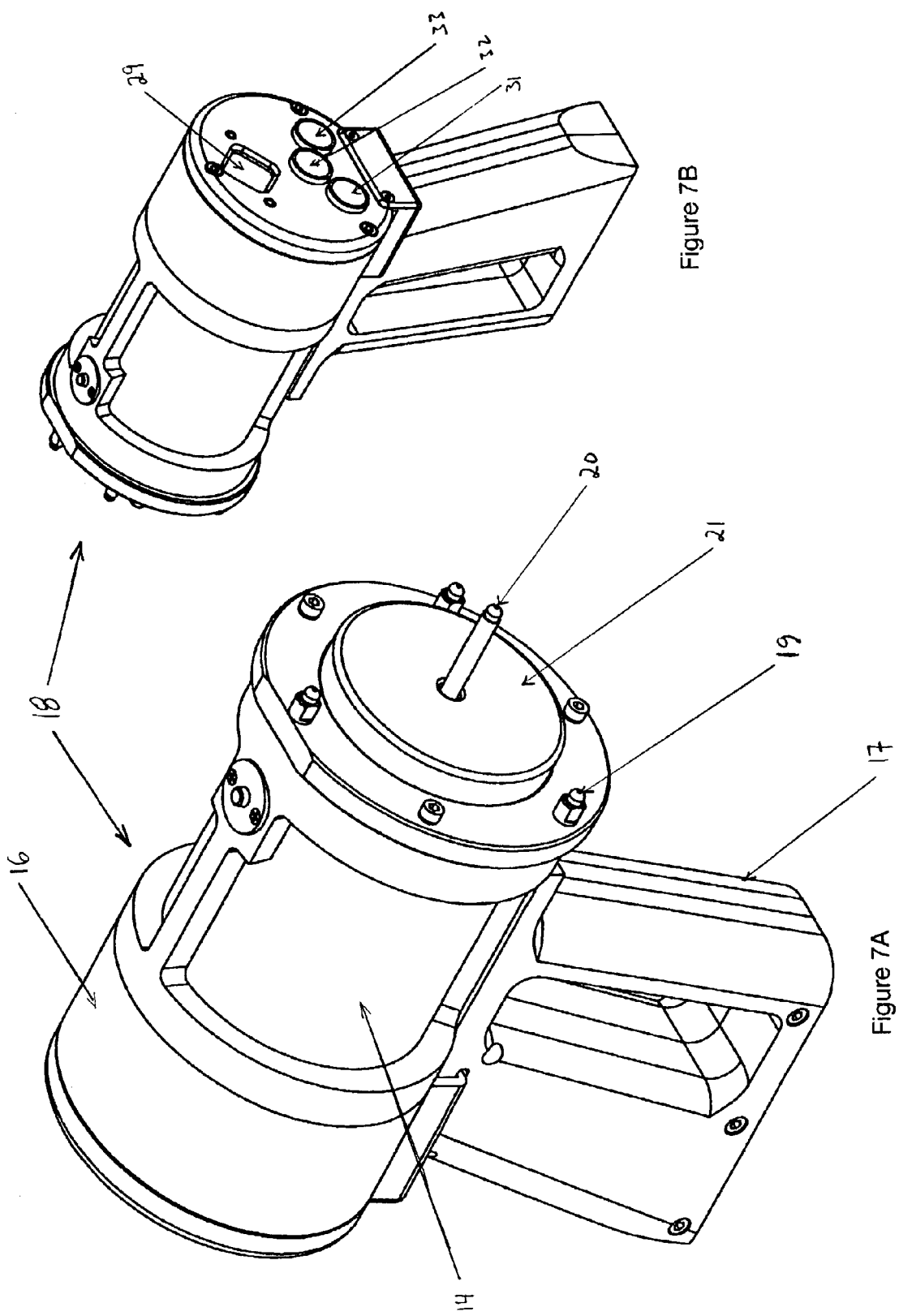
FIG. 7A is a three-dimensional sketch of the phased array probe system showing the probe from the side as in FIG. 5.
FIG. 7B is the same sketch as in FIG. 6A except it is rotated so that the LED centering indicators on the rear face are visible.

FIGS. 7A and 7B are three dimensional views of the PA probe assembly 18 from two different angles, one of which illustrates the back face of the probe.

Boot

Figure 8A:
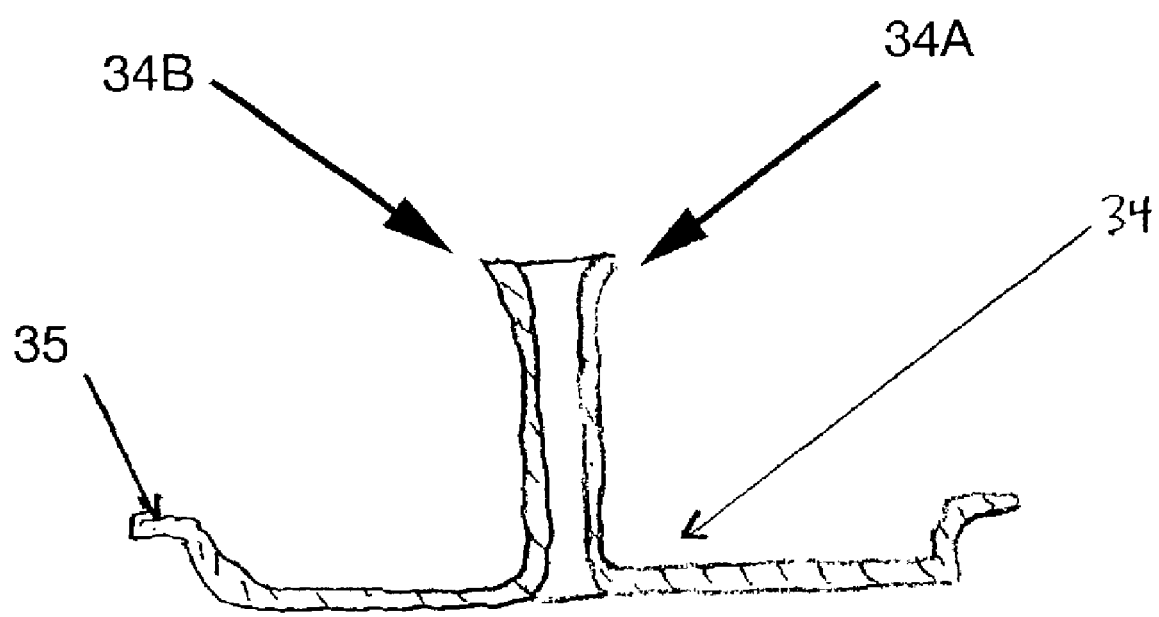
FIG. 8A is a cross section side view of the latex membrane that makes up the boot.
Figure 8B:
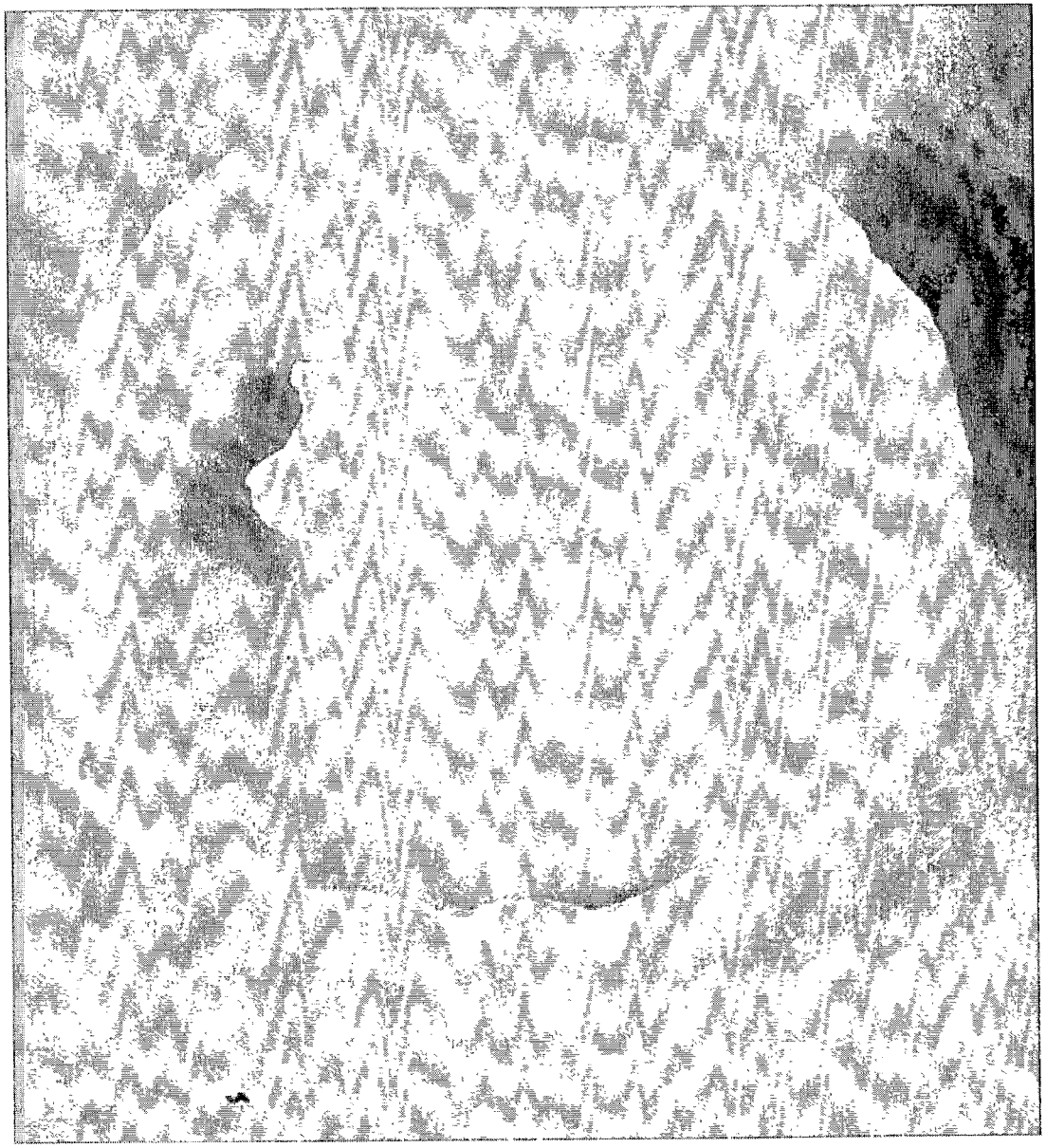
FIG. 8B is a photograph of the membrane of FIG. 8A.
Figure 9:
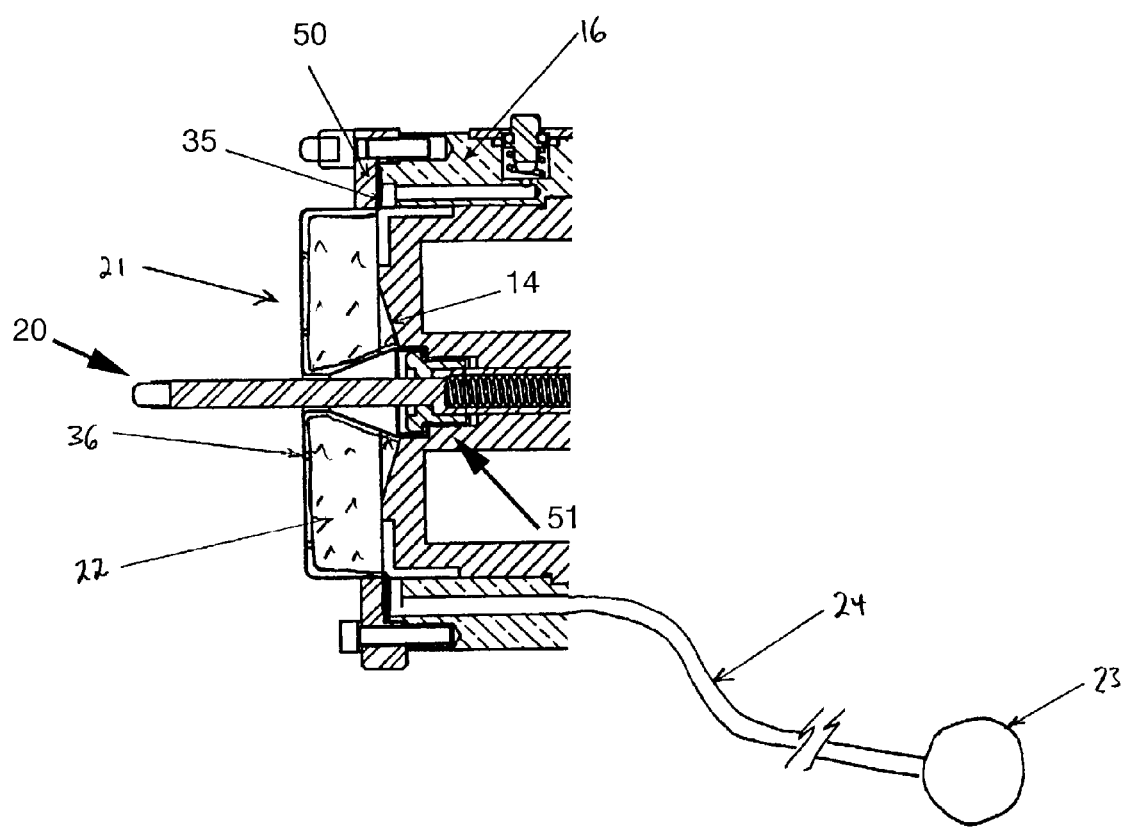
FIG. 9 is an enlarged cross section side view of the forward end of the probe of FIG. 5 showing details of how the membrane of FIGS. 8A and 8B is attached to the probe and filled with coupling fluid.

As depicted in FIG. 5, boot 21 is filled with water, hence it has the appearance of being rigid. In fact, in the preferred embodiment it is made of 0.004 to 0.008 of an inch thick latex by a standard molding procedure and prior to assembly is a quite flexible membrane 34, as can be seen in FIGS. 8A (cross section sketch) and 8B (photograph). It is assembled to the forward end of conical probe 14, as illustrated in FIG. 9 with flange 35 firmly anchored and sealed between housing 16 and ring 50. Boot 21 is donut-like with a central sleeve 34A to receive centering rod 20. Sleeve 34A terminates in a flange 34B that is sealing fitted by insert 51 and housing 16 into the central opening of conical probe 14.

Figure 10:
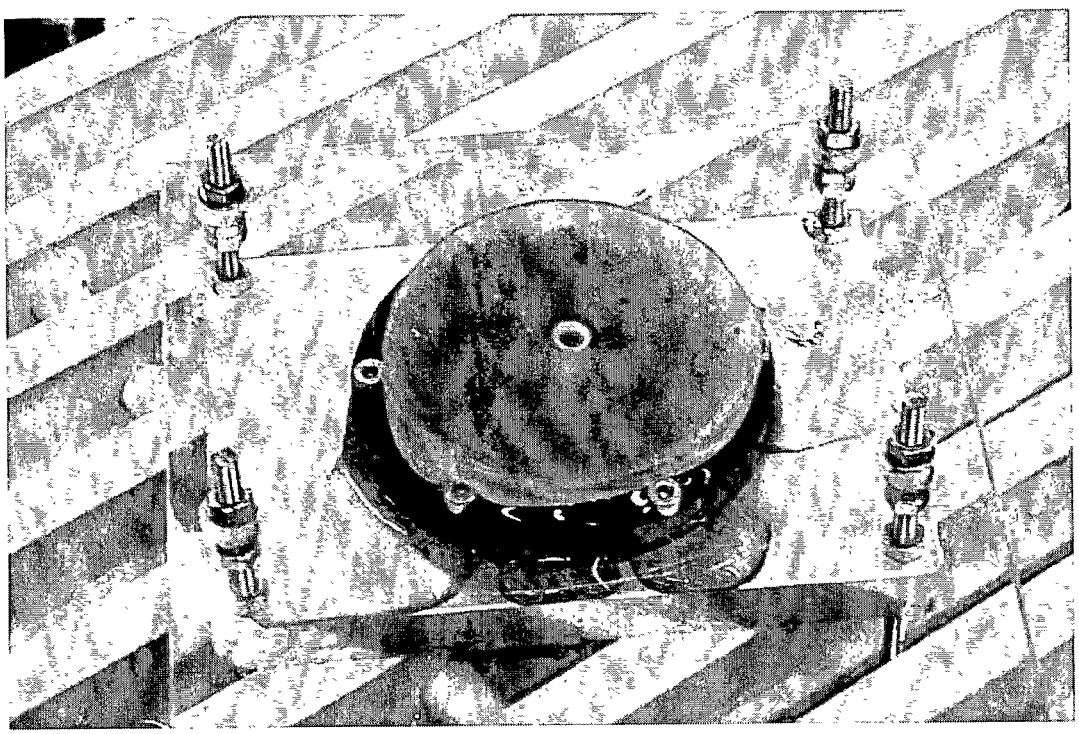
FIG. 10 is a photograph of the boot under pressure showing the deformation of the membrane in simulated operational conditions.

Prior to operation, membrane 34 is filled with coupling fluid 22 (usually water) from pump 23 via channel 24 to form boot 21. Membrane 34 has small perforations 36 in it which allow a small amount of water to pass through it to wet surface 2A (see FIG. 1A) sufficiently to ensure proper acoustic coupling into the metal being inspected. During operation of PA probe assembly 18, membrane 34 of boot 21 is in tight contact with the surface 2A surrounding the fastener hole, thereby deforming membrane 34. The extent of this deformation is shown in FIG. 10, which is a photo of membrane 34 under pressure as seen from the top through a plexiglass plate simulating surface 2A. Water is continuously fed into boot 21 at a low flow rate to compensate for the loss of fluid through perforations 36 and to keep boot 21 full.

Probe Centering

To relax the constraint of having to position the testing device precisely over the center of fastener 1 to be inspected, in the preferred embodiment it is sufficient for the PA probe assembly 18 to be first roughly centered by hand and eye approximation within 0.060 of an inch of the true center of the fastener 1. To assist in the initial manual alignment, PA probe assembly 18 of the invention may optionally be provided with a central, spring-loaded centering rod 20 which may be placed on fasrener head 6 of fastener 1. Depression of this rod into cavity 20A (see FIG. 5) by steady pressure on PA probe assembly 18 will allow said probe to descend upon fastener 1, landing preferably with conical probe 14 approximately positioned centrally over fastener 1. The object of this coarse centering system, with or without centering rod 20, is to position the phased array probe within 0.060 of an inch of the true center of the fastener.

This initial coarse manual centering is followed by a more refined procedure wherein subsequent movement of PA probe assembly 18 by the operator to locate its mechanical center within 0.030 of an inch of the true center of fastener 1 is guided by an electronic feedback system. To achieve this, the center of the fastener is compared with the geometric center of the conical probe 14. Signals are provided to an electronic feedback display (e.g., LED screen 29) that cause the operator to shift the probe towards having its mechanical center coincide with the center of the fastener opening. This electronic feedback system provides the operator with signals that guide said operator in situating the center of PA probe assembly 18 (i.e., the centre of conical probe 14) within 0.030 of an inch from the true center of the fastener opening. Once positioned within this tolerance range, electronic manipulation of the deflection of the ultrasonic beams during inspection is sufficient to accommodate the remaining misalignment. Inspection details are provided in the next section below.

The intersection of the hole with faying surface 37 forms a corner 38, as shown in FIG. 11, which is a good reflector for ultrasonic beams 8. By measuring the time for the beam 8 to go from the conical probe 14 to the corner 38 and return, the distance between the elements 9 in conical probe 14 that formed the beam 8 and the corner 38 can be calculated. As the angles of the beam 8 inside the water 22 and inside the first skin material 2 are known, it is possible to position the corner 38 with respect to the conical probe 14. Measuring the position of at least three points around the circumference 7 of the hole 1 will provide, after calculation, the diameter and centre position of the hole 1.

To provide signals to this operator-assisting electronic feedback system, at least three beams 8 are used to locate points on the cylindrical surface 7 of the fastener opening 1 at a common depth below the surface of the skin within which such opening 1 is formed. Initially, such beams 8 must sweep through the volume of the skin to locate the cylindrical surface 7. Once a scan detects the boundary of the hole 1 by the reflection of ultrasonic beams 8 from the sides of the hole 1, the position of the source of this reflection is recorded as a point on the side of the cylindrical surface 7 of the hole 1. Once three such points have been located, the location of the true center of the hole is determined by applying standard geometric procedures within a computer-based processing controller 25.

Figures 11A, 11B:
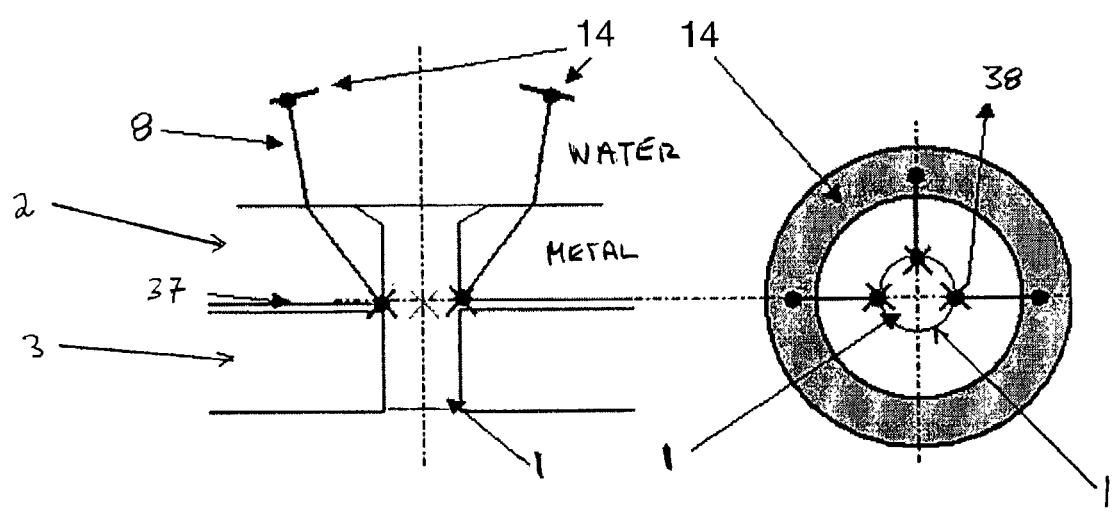
FIG. 11A is a side view of the fastener hole conical probe that illustrates the centering of the probe over the fastener hole.
FIG. 11B is a top view of FIG. 11A.
Figure 11C:
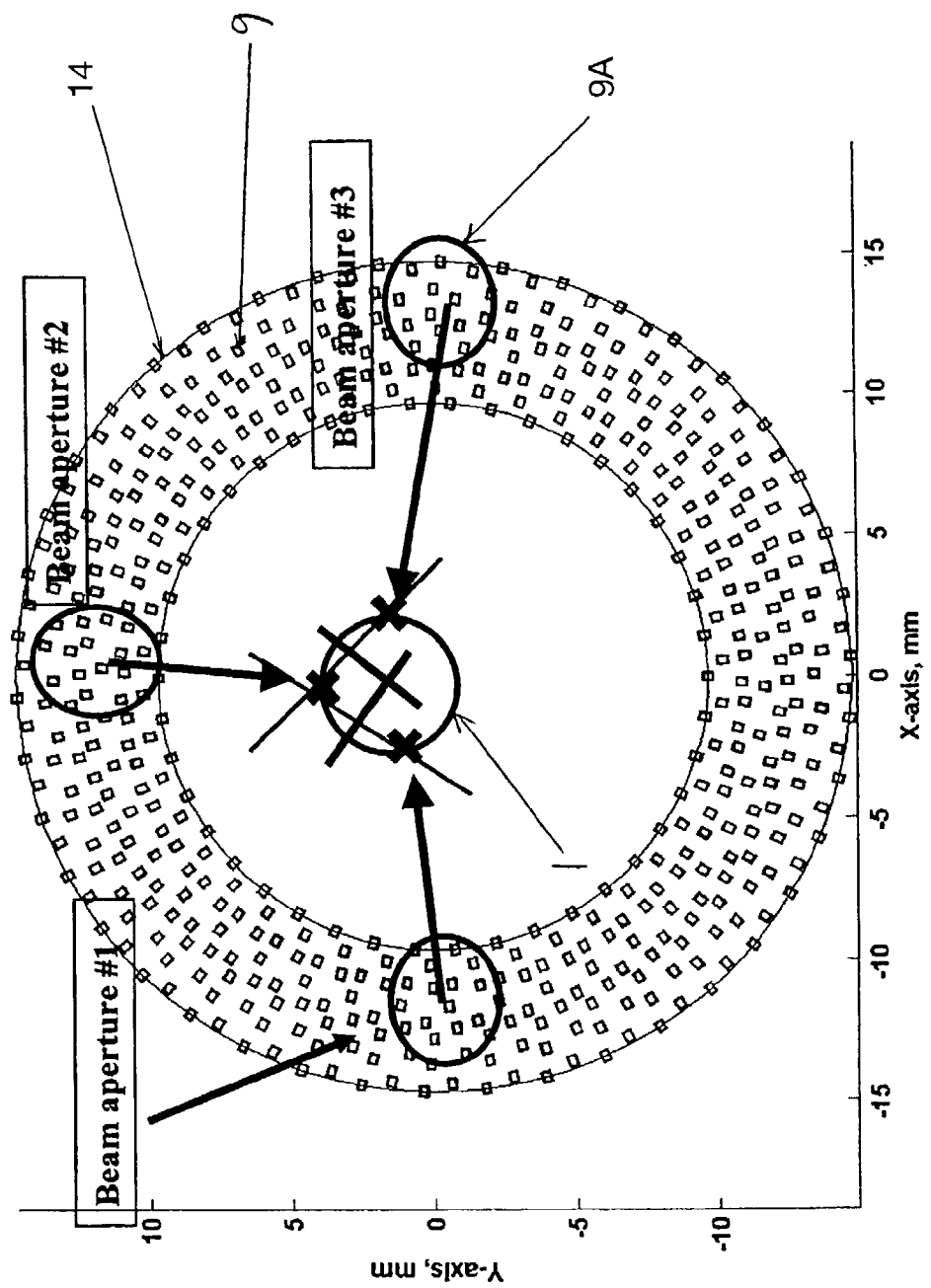
FIG. 11C is a further top view of FIG. 11A giving additional detail of the conical probe.

This is illustrated in FIG. 11A, which depicts a side view of the fastener 1 with conical probe 14 above it; and in FIGS. 11B and 11C, which both depict the top view of FIG. 11A looking down through conical probe 14 at the fastener hole 1 below (FIG. 11C gives additional detail to FIG. 11B). By measuring the position of three points around the circumference 7 of the hole 1 at faying surface 37, the center of the hole 1 can be determined because only one circle passes through the three points. The estimated skin thickness can be calculated as the average thickness of the three different corner positions 38, while the diameter and position of the hole 1 are calculated using a specific algorithm called "best-fit circle".

This algorithm consists in searching for the circle minimizing the mean-square deviation of the distance between all the three points and the circle. In other words, this algorithm consists in growing a circle centred at different positions until it passes through the three points. Using actual computers (1.8 GHz processors), this algorithm can be used in real-time despite its high number of iterations with a greater number of points.

If it were assumed that the fastener hole 1 is perfectly round, only three measurements would be needed to determine the exact location of the center. In reality, however, fastener holes 1 are not perfect, and the system determines a weighted center of the fastener hole 1 by averaging a series of three-point measurements around the faying surface circumference 7. It is important to note that, although the rough centering is done using the fastener head 6 as reference, the final centering is done using the fastener hole circumference 7 at the faying surface 37, which is where the inspection is being performed.

For this system to function properly, calibration for two parameters must be conducted prior to use. First it is necessary to know the "wedge delay", which is the time before the beam 8 enters the metal material, because without it measurements of the hole diameter 1 and depth are not accurate when inspecting off-centered holes. That is, knowing the wedge delay ensures that the system will determine whether the hole is perfectly centered or not. This is done using a pre-centered fastener hole and then modifying on-line the wedge delay until both diameter and depth measurements are identical to those of the calibrated hole. This calibration must be done every day before inspection, and is dependent upon the types of holes to be inspected. It takes only a few minutes.

Second, it is necessary to ensure that the system knows the exact position of the center of the hole when it is off-center. This is done by measuring the position of fastener holes 1 when they are slightly off-center up to 0.060 of an inch away from the center of the conical probe 14. Typical results are analyzed in the three B-scans shown in FIGS. 12A, 12B and 12C.

Figure 12:
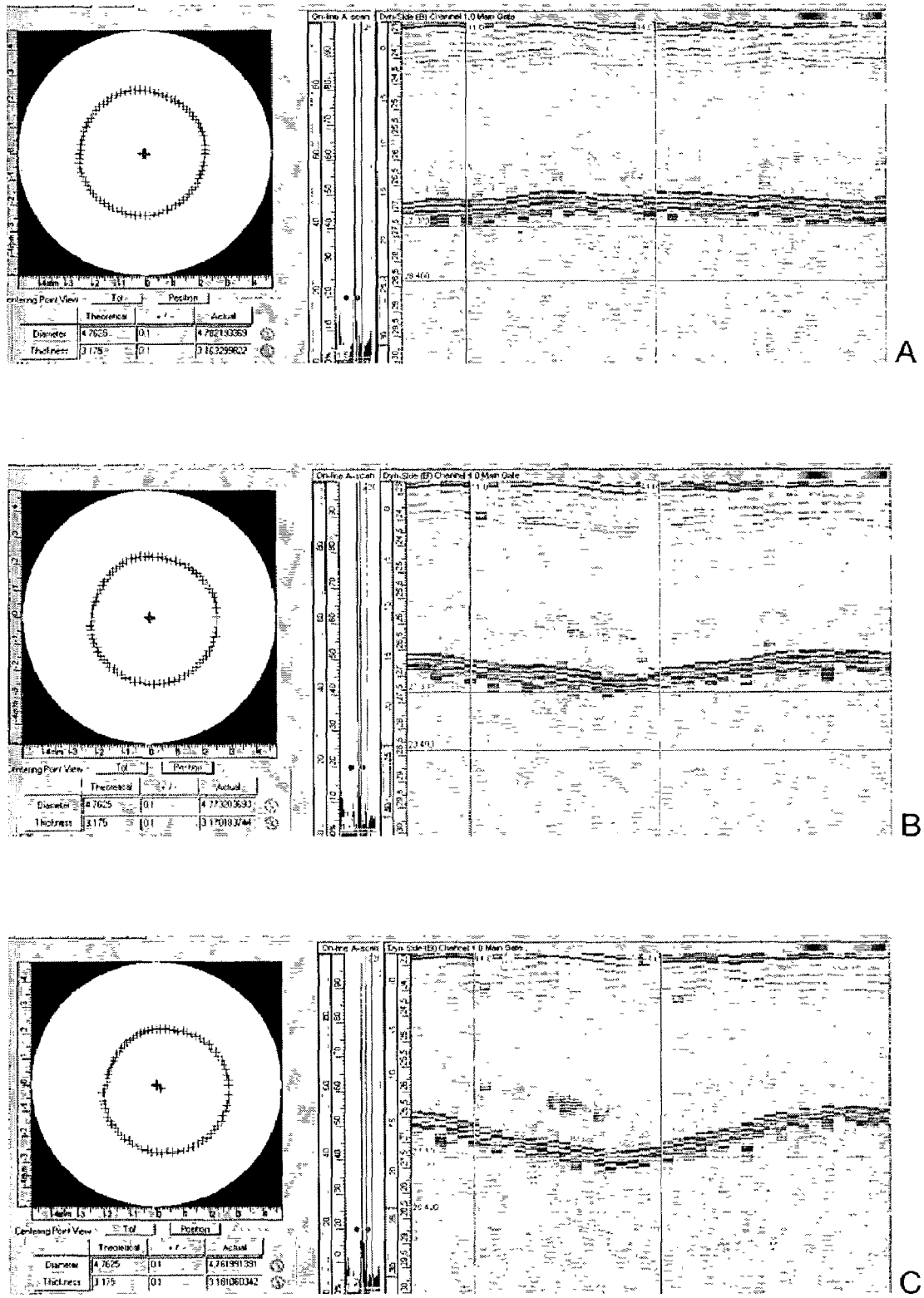
FIG. 12A is a B-Scan for a fastener hole 0.040 of an inch in the northeast direction from the probe center for determination of the distance correction factor (DFC).
FIG. 12B is a B-Scan for a fastener hole 0.030 of an inch in the southwest direction from the probe center for determination of the DFC.
FIG. 12C is a B-Scan for a fastener hole 0.045 of an inch in the southwest direction from the probe center for determination of the DFC.

FIG. 12A is a B-Scan representation of the ultrasonic acquisition with a fastener hole 1 originally positioned in the north-east direction (distance from probe centre is 0.004 of an inch). Even this small deviation can be observed either on the B-Scan display (note the deviation of the time-of-flight curve from a straight line) or on a reconstructed view on the left hand side of the figure. In FIG. 12B, the B-Scan representation is of an ultrasonic acquisition with a fastener hole 1 off-center in the southwest direction (distance from probe centre is 0.030 of an inch). Here the time-of-flight curve is "sinus-shaped". Finally, the B-Scan representation in FIG. 12C is of an ultrasonic acquisition with a fastener hole 1 off-centre in the southwest direction (distance from probe centre is 0.045 of an inch).

Figure 13:
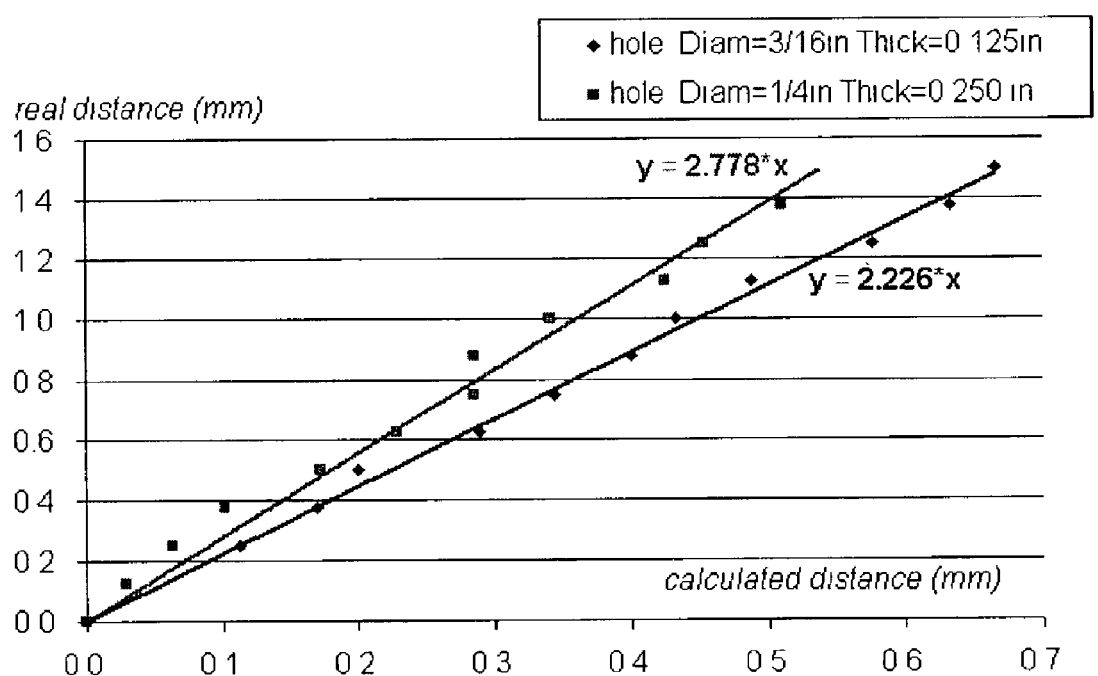
FIG. 13 is a graph correlating real distance with calculated distance for the determination of the DFC.

These results lead to a comparison of the distance measurement versus the real displacement of the hole, as correlated in FIG. 13 for two hole sizes. By interpolating each series of points by a linear curve, a distance correction factor (DCF) can be calculated ensuring a minimal deviation of less than 0.1 mm (DFC=2.778 for a hole diameter of 0.1875 of an inch and a depth of 0.125 of an inch; and DCF=2.26 for a hole diameter of 0.25 of an inch and a depth of 0.25 of an inch). Once the DCF has been calibrated for every type of fastener hole, measurements can be done with accuracy in positioning as tight as 0.1 mm (~0.004 of an inch) with fastener holes as far as 1.5 mm (~0.060 of an inch) from the center of conical probe 14.

With these two calibrations completed, centering is effected by roughly centering the PA probe assembly 18 over the fastener head 2A by hand using the centering rod, if present, as described above. The Centering button 31 on the rear face of probe 18 (see FIG. 6) is then pushed and fine centering is completed interactively by the operator and the probe-centering algorithm described in the previous section.

While a variety of presentation mechanisms may be employed, the preferred embodiment adopts a display in the form of four illuminated sources 29A, 29B, 29C and 29D arranged in the pattern of a cross appearing on LED indicator screen 29. The illumination of a single source provides a signal that the probe assembly should be displaced in the direction of the illumination (e.g., an upper source 29A on the screen 29). When two contiguous sources (e.g., 29B and 29C) are illuminated, a signal is provided that the probe assembly should be displaced in an oblique direction, passing between the two illuminated sources. When all four sources are lit, the operator is informed that centering within preset tolerance limit has been achieved. In this manner, an operator is given a ready indication as to positioning the PA probe assembly 18 substantially centrally over the fastener hole 1 to be inspected. This procedure normally takes less than 15 seconds.

Inspection

Once centering of the probe assembly 18 has been completed within 0.030 of an inch of true center, the Inspection button 32 is pushed to activate a scanning scenario that maps the sides of the hole 1 location and determines whether defects are present at the faying surface 37 surrounding the fastener hole 1. This scenario includes use of a look-up table to download the necessary focal laws, and re-verification of the position of PA probe assembly 18 to ensure that no movement has occurred during the scan. This sequence may be completed in a matter of a few seconds, the data being displayed as a plan view colour map with the fastener hole 1 position indicated and any defects shown along with their relative orientation around the hole 1. The data may also be captured electronically for a separate analysis and display.

The scanning methodology utilizes the fact that small variations in the fastener hole diameter 1, first layer thickness 2 and crack 5 morphology move the "best" interrogation point 39 (IP 39) from the expected intersection of the hole 1 and faying surface 37. A conglomerate technique has been incorporated that interrogates the suspect region from a variety of incident angles and takes several points in the vicinity of the IP 39 as a localized scan. The circumferential scanning, therefore, cuts a volumetric swath around the base of the hole 1 from many different angles, which improves the reliability of the inspection. By perturbating the actual IP 39 about the calculated "ideal" IP, there is a greater chance of getting multiple responses, including the optimal response, from a flaw.

Figure 14:
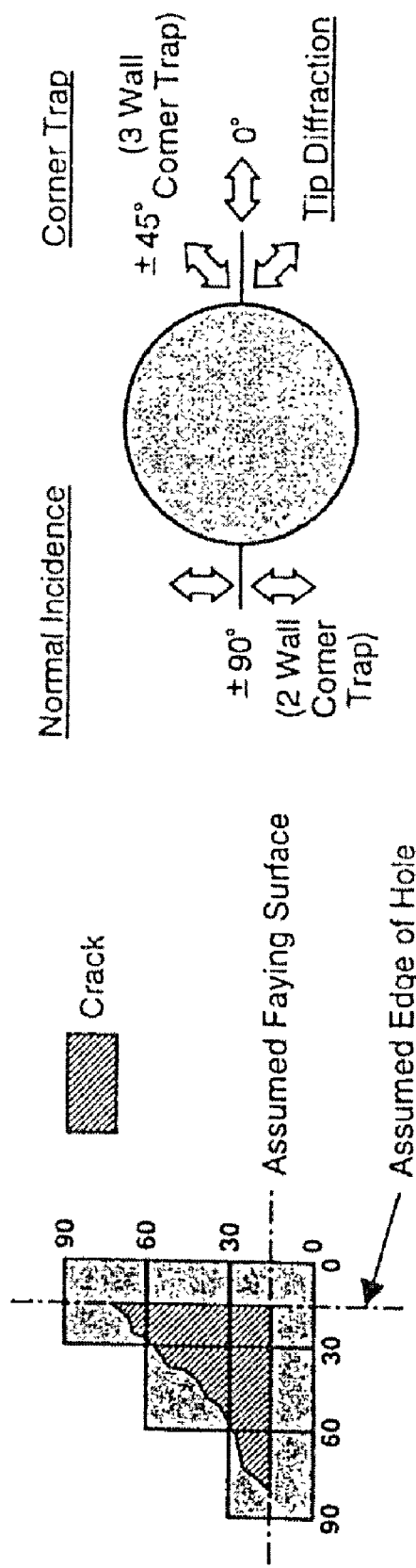
FIG. 14A depicts the local scanning procedure during inspection.
FIG. 14B illustrates the inspection methodology for varying inspection angles.

FIG. 14A shows the principle of local scanning. A pattern of pixel points is chosen adjacent to the assumed location of the defect, which for many inspections is at the intersection of the hole and faying surface. This method has the advantage of defocusing to cover a larger area without the resultant loss of defect response amplitude for small defects.

FIG. 14B demonstrates the principle of using several interrogation angles. This approach uses different sections of the conical PA array to strike the IP in such a way as to generate a two or three wall corner trap, and also to generate a direct response from the tip of a crack, if one is present. In practice, the tip diffraction approach would only be used for characterization and sizing of a crack, but is shown here for completeness.

The number of points chosen for the local scanning and the number of angles chosen is flexible, but hardware limitations and time constraints put an upper limit on the total number of pulses per IP 39. One limitation is that a maximum of 1,024 focal laws may be downloaded for a single fastener hole inspection. Therefore, any combination of points and angles around the circumference cannot exceed this number. For example, a four-point pattern is chosen using four angles for each point. This allows up to 64 IPs around the circumference, or one inspection every 5.63 degrees. Abbreviated inspection sets requiring fewer focal law calculations and downloads are desirable to speed up the inspection process.

A preferred scan pattern is to direct the focal points of three probing beams 8 at consecutive locations encircling the fastener opening. Thus, each scanned location is preferably sampled by three beams arriving at the sampled location along three distinct paths. To maximize the detection of cracks formed around the fastener opening, such beams are preferentially selected to arrive at the scanned location along paths which are generally tangentially oriented with respect to the side of the fastener opening, as illustrated in FIG. 2.

Figure 15:
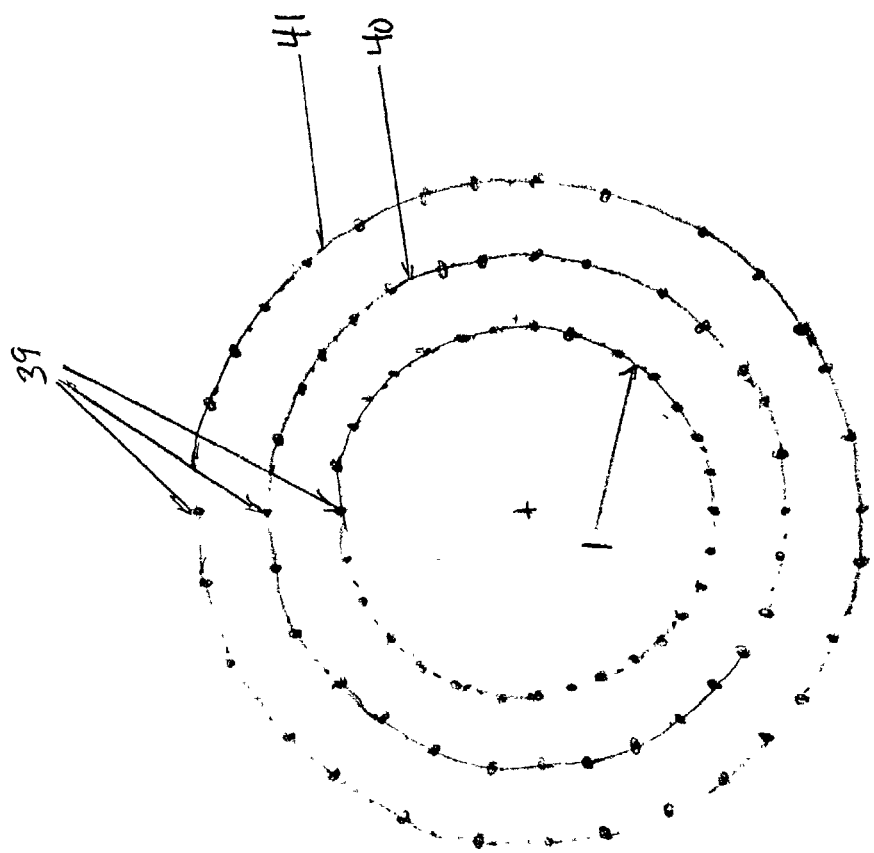
FIG. 15A is a top view looking down on the fastener hole showing the inspection points around the circumference of the hole and the tangential orientation of the inspecting beams during inspection.
FIG. 15B is the same view as in FIG. 15A showing the additional encircling paths upon which scanning is conducted during inspection.
Figure 15:
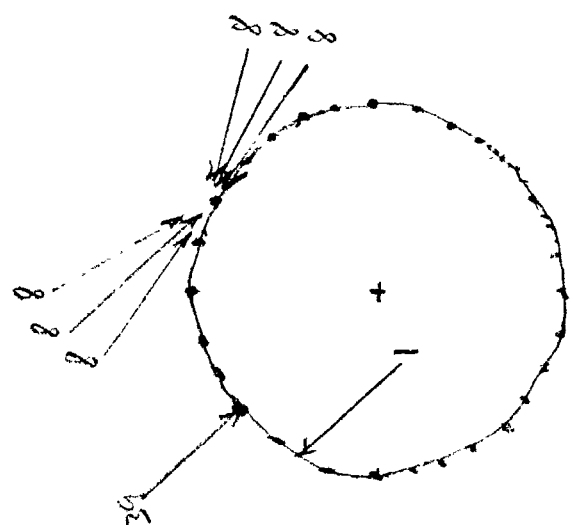

As a preferred procedure, two sets of more than one probing beams 8 are directed to a scanned location from opposite sides of the fastener opening 1, arriving along generally nearly tangential paths. As illustrated in FIG. 15A looking down on the top of the fastener hole 1, more preferably, two sets of three beams 8 are directed to the scanned location (or IP) 39, each set arriving from an opposite side. Thus, a total of six beams 8 are used to sample each IP 39, preferably in a tangential direction with respect to the hole surface 7. Generally, and preferably, the sampled IPs are equally spaced around the cylindrical opening 1, as described above.

This preferred scan pattern may commence initially with a path that follows the circumferential boundary of the cylindrical surface 7 of the hole 1 at the level of the faying surface 37, as illustrated in FIG. 15B by IPs 39 around fastener 1. The number of IPs 39 shown is illustrative only and does not represent the exact number of IPs. Second and, optionally, scanning patterns are then preferably directed along encircling paths 40 and 41 located at progressively greater radius from the center of the fastener opening. The number of encircling paths 40,41 is discretionary. Then optionally, and preferably, these IPs 29 may be located radially outwardly from the initial inspected points positioned around the side surface 1 of the hole.

The described procedure results in a multi-angle, multi-positional inspection strategy that has been found to efficiently increase the probability of locating a defect.

Displaying the Scan Data

Figure 16:
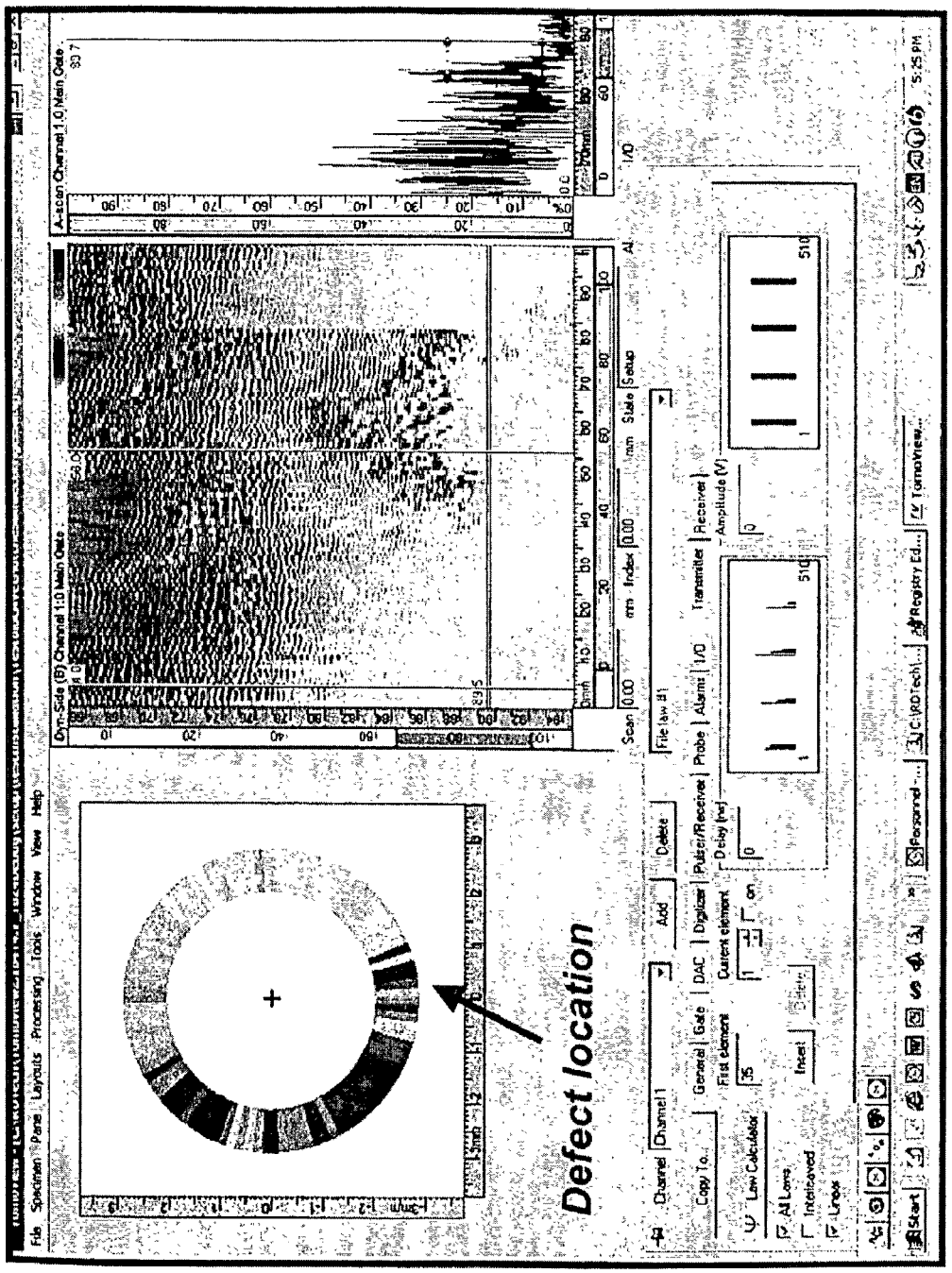
FIG. 16 is an example of the inspection screen showing a defect.

Displays of each angle and location would be cumbersome and difficult to interpret, so the peak response data from each pulse is saved and merged into a single value for each IP 39. This merged data approach greatly simplifies data presentation and interpretation. A colour display similar to a C-Scan image is used to represent the IPs 39 about the circumference 7 of the hole 1. A grayscale representation of this simplified display is shown on the left of FIG. 16, which is an example of the inspection screen. In the colour display, the defect location is clearly indicated as a red sector (not evident in the grayscale image). Each sector of this display represents the maximum peak value of all of the angles and locations in the interrogation set for that IP 39. Different merging parameters, such as the average value of the sum of all the values, can be shown as well, as in the center and right hand parts of the screen.

Defect Characterization

Figure 17:
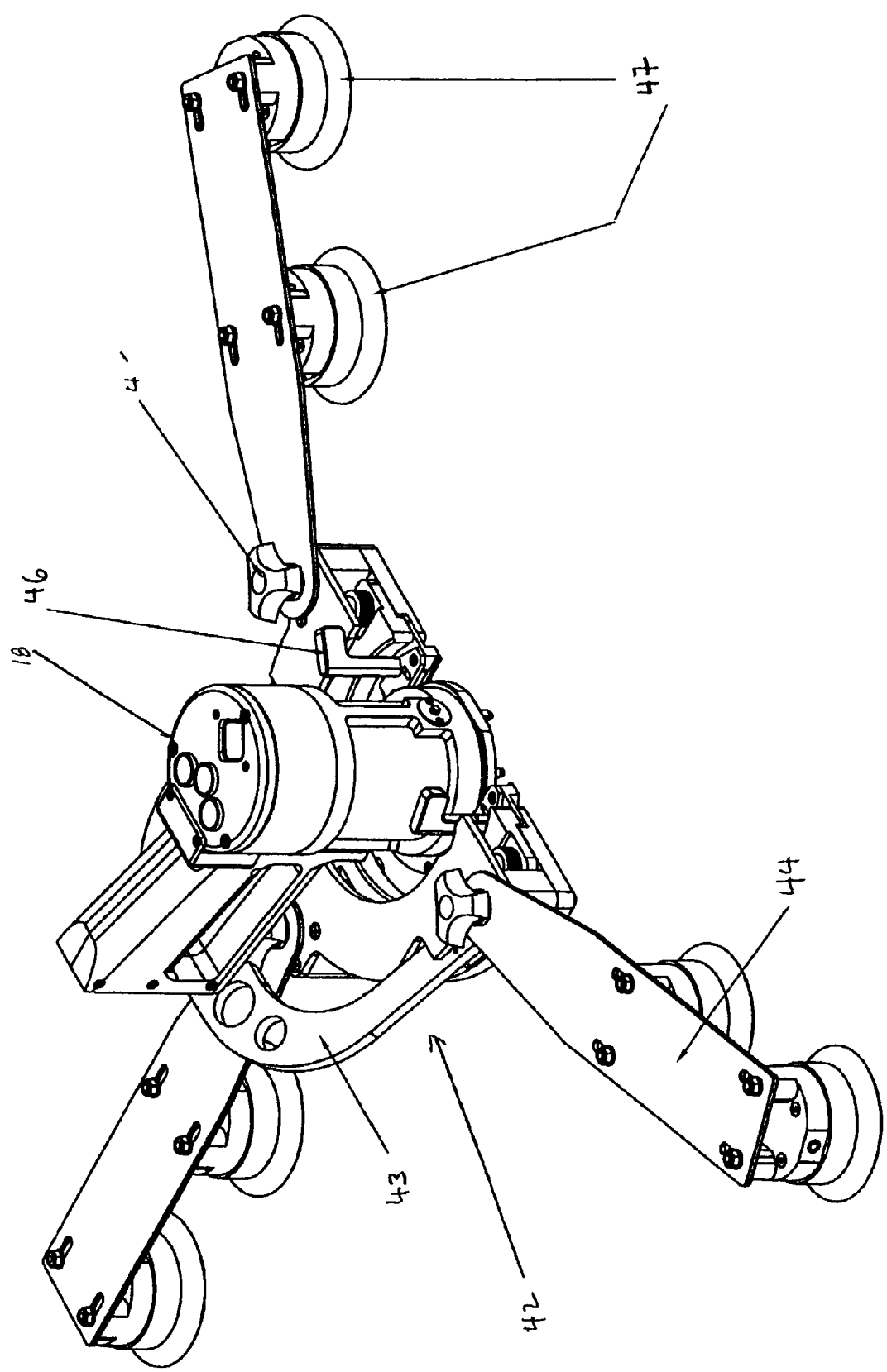
FIG. 17 shows the mounting fixture holding the PA probe motionless during a defect characterization process.

While the inspection itself, with electronic scanning, takes only a fraction of a second, focal law calculation can take several seconds. Once an indication of the possible presence of a defect has been detected, the full power of the system can be utilized to evaluate a smaller region around the possible defect location. During this interrogation, the PA probe assembly 18 can be attached, for example, to an aircraft wing containing the fastener hole 1 under inspection, with mounting fixture 42, as shown in FIG. 17. A new group of up to 1,024 focal laws can be downloaded to interrogate a much smaller volume, thereby allowing more angles and finer increments to be used.

Mounting fixture 42 ensures that PA probe assembly 18 remains motionless during the time it takes to characterize a defect, which is considerably longer than the detection procedure (possibly up to a few minutes). Fixture 42 is positioned over the fastener hole 1 under inspection by manipulating tripod arms 44 before tightening knobs 45 and then rigidly attaching everything to the wing by engaging vacuum cups 47. Next, PA probe assembly 18 is placed into the brake shoe controlled by brake lever 43, but brake lever 43 remains disengaged so that fine positioning of PA probe assembly 18 can be effected following the centering procedure detailed above. Once PA probe assembly 18 is centered, brake lever 43 is tightened and the characterization procedure commences.

Test Fixture

Figure 18:
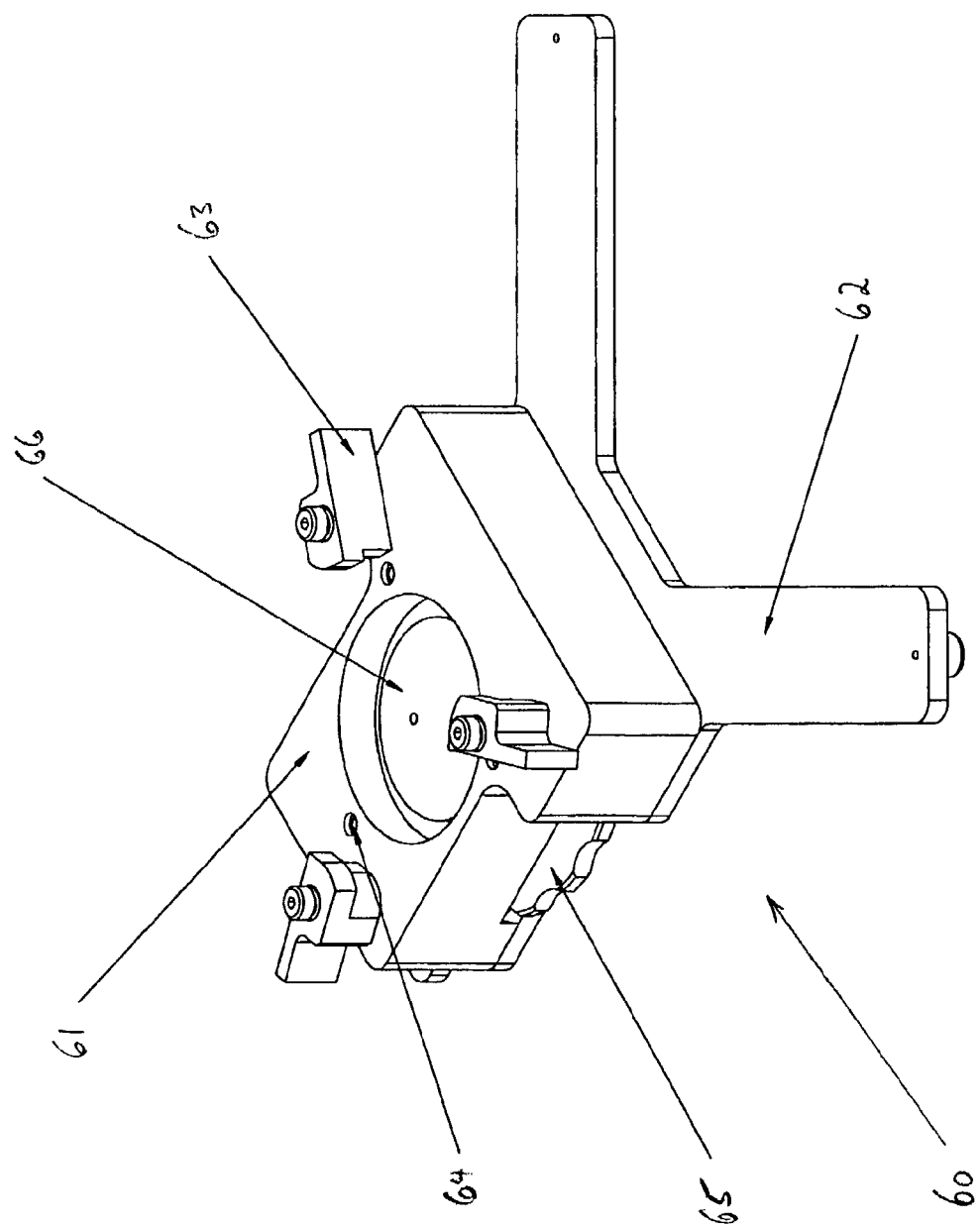
FIG. 18 is a three-dimensional sketch of the multi-functional test fixture.
Figure 19:
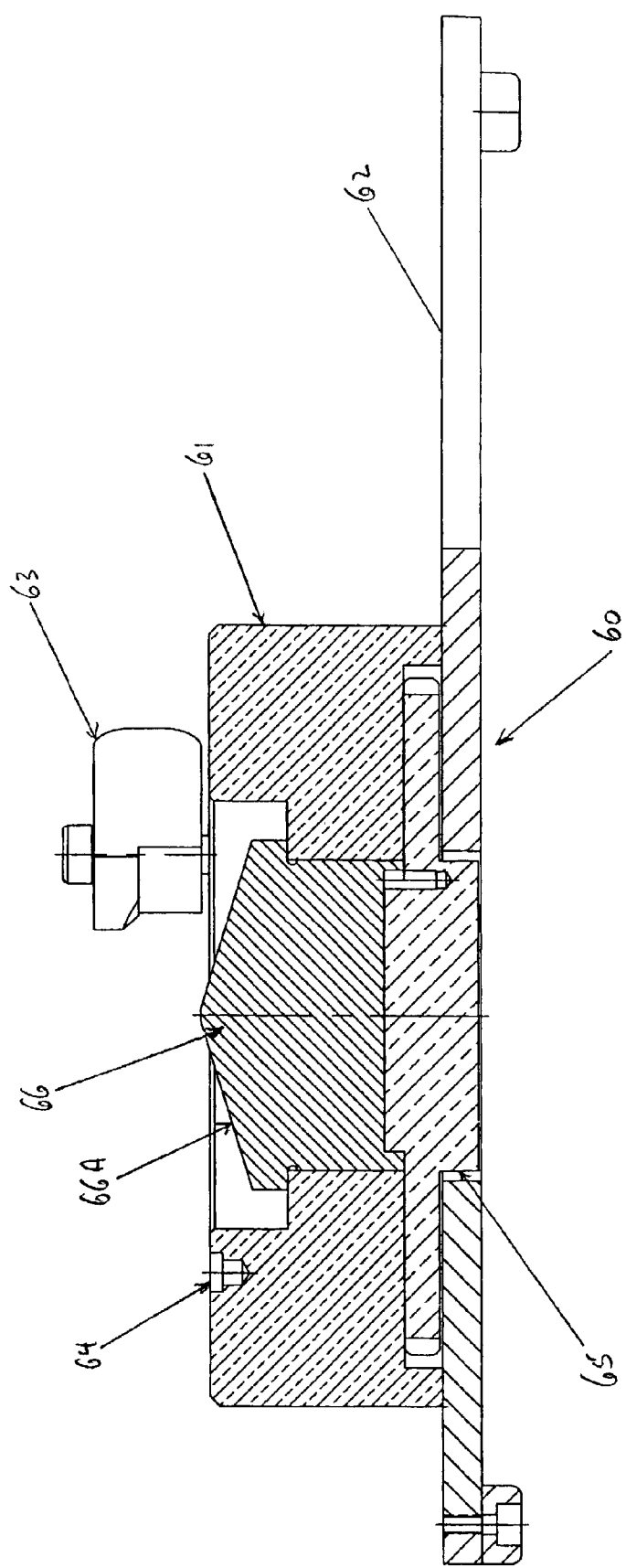
FIG. 19 is a cross section view from the side of FIG. 18 showing the functionality test block in position.

As illustrated in FIG. 18, multi-functional test fixture 60 comprises probe support body 61 on tripod 62 with spring-loaded clamp 63, socket 64 and rotary dial 65. Removable test block 66, which is shown in cross section in FIG. 19, is a conically shaped target having a target surface 66A having the same angle as conical probe 14 of PA probe assembly 18.

Figure 20:
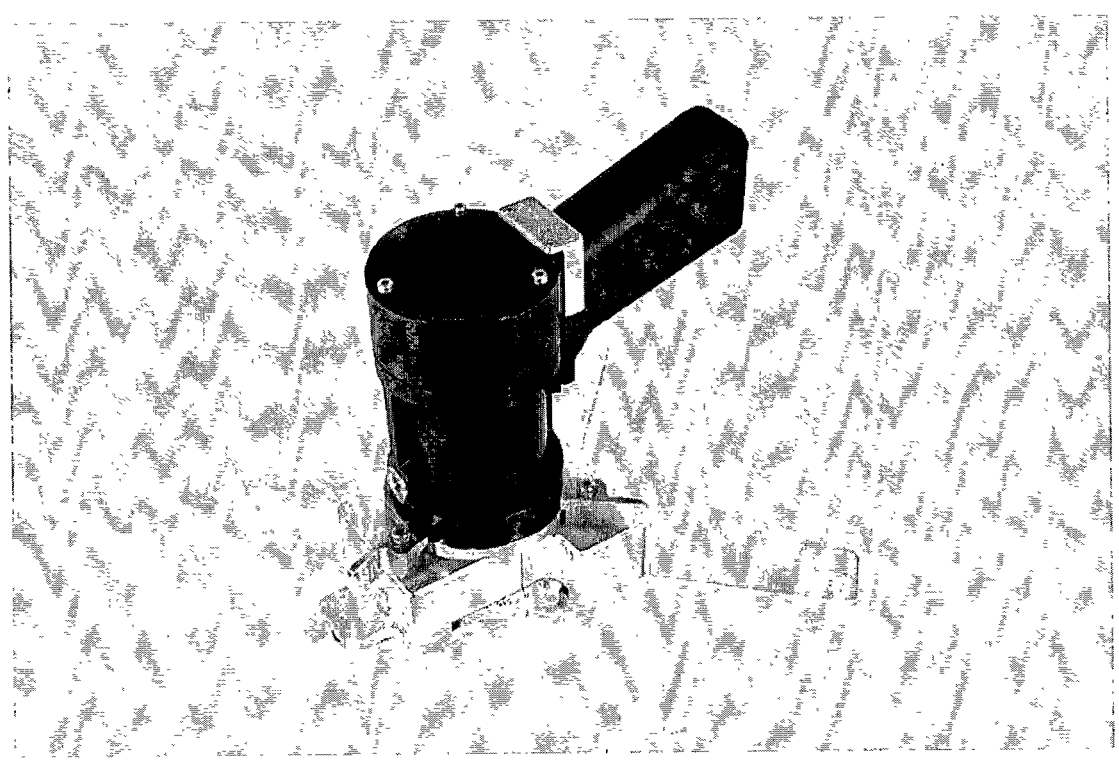
FIG. 20 is a photograph of the PA probe assembled in the test fixture.

Test fixture 60 is used for two different tests, the first of which is to verify the functionality of conical array 10 using test block 66. To do this, PA probe assembly 18 is fitted over test fixture 60 as shown in the photograph of FIG. 20, being centered by placing feet 19 into sockets 64 and then being firmly held in position by clamps 63. The test fixture and the forward end of PA probe assembly 18 are then immersed in a water bath to a depth that ensures that conical probe 14 is underwater during the period of testing.

To verify the functionality of conical probe 14, system controller 25 sequentially activates elements 9 of said probe so that precise data may be obtained from the conical target surface 66A. This data can be used to ensure that the individual elements 9 are functioning properly as well as electronically correcting for slight misalignments or mispositioning of said elements 9 in the conical probe 14. The system is also able to compensate for variations in element 9 sensitivity by applying corrections to the received signal for each element 9.

Figure 21:
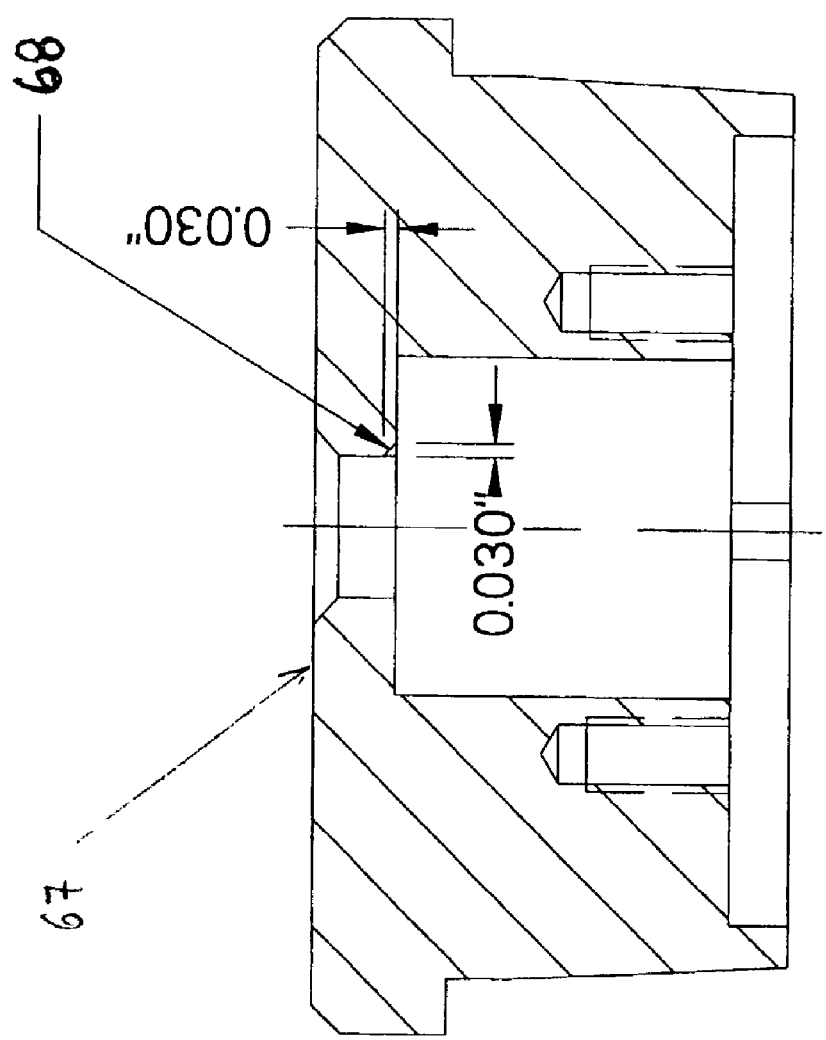
FIG. 21 is a cross section of a typical notch test block.

The second test for which test fixture 60 is used is that to verify the uniformity of response of conical probe 10 to cracks at various locations around the fastener hole 1. Other test blocks, as typified by test block 67 shown in cross section in FIG. 21, are inserted into test fixture 60 in place of conical test block 66. Test block 67, for example, has a standard EDM notch 68 (0.030 of an inch by 0.030 of an inch by 0.008 of an inch wide). Such test blocks can then be rotated through 360 degrees using rotary dial 65 so that the same defect is sequentially detected by different parts of conical probe 14. If the response is not uniform at all test locations, electronic corrective actions may be taken by the system controller 25 to adjust apparent signals obtained in the field in accordance with the calibration data obtained from these tests.

CONCLUSION

Advantages of this system of the invention are that it to need not contain any moving parts. It may be constructed in a light compact format. Using rapid electronic phased-controlled scanning permits testing to be completed within less than a minute. Three-dimensional beams steering allows great flexibility in scanned patterns, contributing to improve reliability.

The foregoing has constituted a description of specific embodiments showing how the invention may be applied and put into use. These embodiments are only exemplary. The invention in its broadest, and more specific aspects is further described and defined in the claims which now follow.

These claims, and the language used therein, are to be understood in terms of the variants of the invention that have been described. They are not to be restricted to such variants, but are to be read as covering the full scope of the invention as is implicit within the invention and the disclosure that has been provided herein.

The embodiments of the invention in which an exclusive property or privilege is claimed are defined as follows:

1. An ultrasonic probe assembly suitable for detecting defects in material surrounding a fastener hole, the probe comprising:
    an array having a plurality of ultrasonic elements disposed circumferentially around an axis;
    at least one controller to drive the ultrasonic elements;
    a centering procedure to be used by the at least one controller for driving the plurality of ultrasonic elements to generate at least three probing beams directed at the material surrounding the fastener hole, said at least three probing beams providing information by reflection of the at least three probing beams into the ultrasonic elements to determine the location of the fastener hole center, said centering procedure corresponding to a first mode of operation;
    a set of focal laws defining a scanning procedure to be used by the at least one controller for driving the plurality of ultrasonic elements to generate at least two probing beams directed at the material surrounding the fastener hole, said at least two probing beams providing information by reflection of said at least two probing beams into the ultrasonic elements, said scanning procedure corresponding to a second mode of operation;
    a selector for selecting between the first and the second modes of operation; and
    an output to provide information resulting from the propagation of the at least three or two probing beams in the selected first or second mode of operation; and
    wherein selection of one mode of operation provides different information than selection of another mode of operation.

2. An ultrasonic probe assembly as defined in claim 1 wherein the plurality of ultrasonic elements are disposed in pseudo-random groups.

3. An ultrasonic probe assembly as defined in claim 1 further comprising an interface filled with a coupling fluid, the interface being positioned between the ultrasonic probe assembly and said material.

4. An ultrasonic probe assembly as defined in claim 1 wherein the set of focal laws defines a scanning procedure comprising a pattern of three probing beams arriving along three different paths at a location on the material surrounding the fastener hole, the pattern being repeated for consecutive locations encircling the fastener hole, wherein the pattern of three probing beams form said at least two probing beams of the second mode of operation.

5. An ultrasonic probe assembly as defined in claim 1 wherein said at least two probing beams of the second mode of operation folow paths that are generally tangentially oriented with respect to a side of the fastener hole.

6. An ultrasonic probe assembly as defined in claim 1 wherein the set of focal laws defines a scanning procedure comprising a pattern of two sets of at least two probing beams directed from opposite sides of the fastener hole, the two sets of at least two probing beams forming said at least two probing beams of the second mode of operation and the at least two probing beams of each set arriving along generally tangential paths at a scan location on the material surrounding the fastener hole, the pattern of two sets of at least two probing beams being repeated for consecutive locations encircling the fastener hole.

7. An ultrasonic probe assembly as defined in claim 1 wherein the centering procedure uses a "best-fit circle" algorithm to determine the location of the fastener hole center.

8. An ultrasonic probe assembly as defined in claim 1 wherein the centering procedure uses the coordinates of each of the at least three probing beams in at least three locations around the circumference of the fastener hole to compute the diametric and center coordinates of a circle minimizing the square deviation of the distance between all three locations.

9. An ultrasonic probe assembly as defined in claim 1 wherein the output in the first mode of operation comprises an operator assisting positioning system comprising:
- a plurality of illumination sources arranged in a directional pattern;
- means to illuminate a single source to provide a signal indicating a direction that the probe assembly should be moved to achieve a more near centering of the probe assembly axis over the fastener hole center; and
- means to illuminate all sources when centering of the probe assembly axis over the fastener hole center has been achieved within a preset tolerance limit.

10. An ultrasonic assembly as defined in claim 9 further comprising means to illuminate two contiguous sources to provide an indication that the probe assembly should be displaced in an oblique direction passing between the two illuminated sources.

11. An ultrasonic probe assembly as defined in claim 1 further comprising a means for pre-centering the probe assembly.

12. An ultrasonic probe assembly as defined in claim 11 wherein the means for pre-centering the probe assembly is a centrally positioned centering rod for placement on the fastener, the rod 13. An ultrasonic probe assembly as defined in claim 4, wherein the pattern of the three probing beams follows paths that are generally tangentially oriented with respect to a side of the fastener hole.

14. A method of detecting defects in material surrounding a fastener hole, the method comprising:
- providing an array having a plurality of ultrasonic elements disposed circumferentially around an axis;
- providing at least one controller to drive the ultrasonic elements;
- selecting between a first and a second mode of operation;
- upon selection of the first mode of operation, activating a centering procedure in the at least one controller for driving the plurality of ultrasonic elements to generate at least three probing beams directed at the material surrounding the fastener hole, said at least three probing beams providing information by reflection of the at least three probing beams into the ultrasonic elements to determine the location of the fastener hole center;
- upon selection of a second mode of operation, downloading into the at least one controller a set of focal laws defining a scanning procedure driving the plurality of ultrasonic elements and thereby generate at least two probing beams directed at the material surrounding the fastener hole, said at least two probing beams providing information by reflection of the at least two probing beams into the ultrasonic elements;
- providing information resulting from the propagation of the at least three or two probing beams in the selected first or second mode of operation; and
- wherein selection of one mode of operation provides different information than selection of another mode of operation.

15. A method of detecting defects in material surrounding a fastener hole as defined in claim 14 wherein the plurality of ultrasonic elements are disposed in pseudo-random groups.

16. A method of detecting defects in material surrounding a fastener hole as defined in claim 14 further comprising the positioning of an interface filled with a coupling liquid between the array of ultrasonic elements and said material.

17. A method of detecting defects in material surrounding a fastener hole as defined in claim 14 wherein the set of focal laws defines a scanning procedure comprising a pattern of three probing beams arriving along three different paths at a location on the material surrounding the fastener hole, the pattern being repeated for consecutive locations encircling the fastener hole, wherein the pattern of three probing beams form said at least two probing beams of the second mode of operation.

18. A method of detecting defects in material surrounding a fastener hole as defined in claim 14 wherein said at least two probing beams of the second mode of operation follow paths that are generally tangentially oriented with respect to a side of the fastener hole.

19. A method of detecting defects in material surrounding a fastener hole as defined in claim 14 wherein the set of focal laws defines a scanning procedure comprising a pattern of two sets of at least two probing beams directed from opposite sides of the fastener hole, the two sets of at least two probing beams forming said at least two probing beams of the second mode of operation and the at least two probing beams of each set arriving along generally tangential paths at a scan location on the material surrounding the fastener hole, the pattern being repeated for consecutive locations encircling the fastener hole.

20. A method of detecting defects in material surrounding a fastener hole as defined in claim 14 wherein the centering procedure uses a "best-fit circle" algorithm to determine the location of the fastener hole center.

21. A method of detecting defects in material surrounding a fastener hole as defined in claim 14 wherein the centering procedure uses the coordinates of each of the at least three probing beams in at least three locations around the circumference of the fastener hole to compute the diametric and center coordinates of a circle minimizing a square deviation of a distance between all three locations.

22. A method of detecting defects in material surrounding a fastener hole as defined in claim 14 further comprising the positioning of an interface filled with a coupling liquid between the ultrasonic array and the material surrounding the fastener hole.

23. A method of detecting defects in material surrounding a fastener hole as defined in claim 14 further comprising:
- providing a plurality of illumination sources arranged in a directional pattern;
- indicating a direction that the array of ultrasonic elements should be moved to achieve a more near centering of the ultrasonic array axis over the fastener hole by illuminating a single source;
- illuminating all sources when centering of the ultrasonic array axis over the fastener hole center has been achieved within a present tolerance level.

24. A method of detecting defects in material surrounding a fastener hole as defined in claim 23 further comprising the illumination of two contiguous sources to provide an indication that the array of ultrasonic elements should be displaced in an oblique direction passing between the two illuminated sources. being resiliently depressible into the probe assembly to assist in an initial alignment.

25. A method of detecting defects in material surrounding a fastener hole as defined in claim 14 further comprising a means for pre-centering the array of ultrasonic elements.

26. A method of detecting defects in material surrounding a fastener hole as defined in claim 25 wherein the means for pre-centering the array of ultrasonic elements is a centrally positioned centering rod for placement on a fastener, the rod being resiliently depressible to assist in an initial alignment.

27. A method of detecting defects in material surrounding a fastener hole as defined in claim 17, wherein the pattern of the three probing beams follows paths that are generally tangentially oriented with respect to a side of the fastener hole.

* * * * *